United States Patent
Apte et al.

(10) Patent No.: US 10,388,407 B2
(45) Date of Patent: *Aug. 20, 2019

(54) METHOD AND SYSTEM FOR CHARACTERIZING A HEADACHE-RELATED CONDITION

(71) Applicant: uBiome, Inc., San Francisco, CA (US)

(72) Inventors: Zachary Apte, San Francisco, CA (US); Jessica Richman, San Francisco, CA (US); Daniel Almonacid, San Francisco, CA (US); Rodrigo Ortiz, San Francisco, CA (US); Catalina Valdivia, San Francisco, CA (US); Inti Pedroso, San Francisco, CA (US); Paz Tapia, San Francisco, CA (US)

(73) Assignee: uBiome, Inc., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/819,190

(22) Filed: Nov. 21, 2017

(65) Prior Publication Data

US 2018/0102187 A1   Apr. 12, 2018

Related U.S. Application Data

(63) Continuation-in-part of application No. 15/606,743, filed on May 26, 2017, which is a continuation of application No. 14/919,614, filed on Oct. 21, 2015, now Pat. No. 9,703,929.

(60) Provisional application No. 62/066,369, filed on Oct. 21, 2014, provisional application No. 62/087,551, filed on Dec. 4, 2014, provisional application No. 62/092,999, filed on Dec. 17, 2014, provisional application No. 62/147,376, filed on Apr. 14, 2015, provisional application No. 62/147,212, filed on Apr. 14, 2015, provisional application No. 62/147,362, filed on Apr. 14, 2015, provisional application No. 62/146,855, filed on Apr. 13, 2015, provisional application No. 62/206,654, filed on Aug. 18, 2015, provisional application No. 62/424,717, filed on Nov. 21, 2016.

(51) Int. Cl.
| | | |
|---|---|---|
| G01N 33/48 | (2006.01) | |
| G16H 10/40 | (2018.01) | |
| G16H 15/00 | (2018.01) | |
| G16B 50/00 | (2019.01) | |
| C12Q 1/6883 | (2018.01) | |
| C12Q 1/689 | (2018.01) | |
| G06F 19/00 | (2018.01) | |
| G16B 99/00 | (2019.01) | |
| G06G 7/58 | (2006.01) | |

(52) U.S. Cl.
CPC ............ *G16H 10/40* (2018.01); *C12Q 1/689* (2013.01); *C12Q 1/6883* (2013.01); *G06F 19/30* (2013.01); *G06F 19/3418* (2013.01); *G16B 50/00* (2019.02); *G16B 99/00* (2019.02); *G16H 15/00* (2018.01); *C12Q 2600/118* (2013.01); *Y02A 90/26* (2018.01)

(58) Field of Classification Search
None
See application file for complete search history.

(56) References Cited

U.S. PATENT DOCUMENTS

| | | | |
|---|---|---|---|
| 6,033,864 A | 3/2000 | Braun et al. | |
| 6,309,643 B1 | 10/2001 | Braun et al. | |
| 6,632,641 B1 | 10/2003 | Brennan et al. | |
| 6,861,053 B1 | 3/2005 | Lin et al. | |
| D521,843 S | 5/2006 | Hung | |
| 7,048,906 B2 | 5/2006 | Lin et al. | |
| 7,176,002 B2 | 2/2007 | Lao et al. | |
| 8,478,544 B2 | 7/2013 | Colwell et al. | |
| 8,598,203 B2 | 12/2013 | Tarcic et al. | |
| 8,883,264 B2 | 11/2014 | Yang et al. | |
| 9,028,841 B2 | 5/2015 | Henn et al. | |
| 9,149,473 B2 | 10/2015 | Ecker et al. | |
| 9,433,651 B2 | 9/2016 | Jones et al. | |
| 9,506,109 B2 | 11/2016 | Savelkoul et al. | |
| 9,663,831 B2 | 5/2017 | Apte et al. | |
| 9,703,929 B2 | 7/2017 | Apte et al. | |
| 2002/0012926 A1 | 1/2002 | Quake et al. | |
| 2003/0190314 A1 | 10/2003 | Campbell et al. | |

(Continued)

FOREIGN PATENT DOCUMENTS

| | | |
|---|---|---|
| CN | 105407728 | 3/2015 |
| EP | 2631240 | 8/2013 |

(Continued)

OTHER PUBLICATIONS

"K03100: IepB: signal peptidase I," KEGG, Aug. 7, 2012 (Aug. 7, 2012), p. 1 0f 1. Retrieved from the Internet: on Jun. 12, 2016 (Jun. 12, 2016).

"KEGG: Aminoacyl-tRNA biosynthesis—Reference pathway," Jul. 20, 2013 (Jul. 20, 2013). Retrieved from the internet: <http://web:archive.org/web/20130720015616/http:www.genome.jp/kegg-bin/show_pathway?map=map00970&show_description=show. on Jun. 20, 2016 (Jun. 20.

(Continued)

*Primary Examiner* — Eric S Dejong
(74) *Attorney, Agent, or Firm* — Kilpatrick Townsend & Stockton LLP

(57) ABSTRACT

Embodiments of a method and/or system for characterizing a headache-related condition for a user can include one or more of: generating a microbiome dataset for each of an aggregate set of biological samples associated with a population of subjects, based on sample processing of the biological samples; processing a supplementary dataset associated with one or more headache-related conditions for the set of users; and performing a characterization process for the one or more headache-related conditions, based on the supplementary dataset and microbiome features extracted from the microbiome dataset.

20 Claims, 10 Drawing Sheets

(56) References Cited

U.S. PATENT DOCUMENTS

| | | |
|---|---|---|
| 2005/0196785 A1 | 9/2005 | Quake et al. |
| 2006/0073501 A1 | 4/2006 | Van Den Boom et al. |
| 2006/0089310 A1 | 4/2006 | Goldstein et al. |
| 2007/0054843 A1 | 3/2007 | Yeomans et al. |
| 2007/0134652 A1 | 6/2007 | Slepnev et al. |
| 2007/0259337 A1 | 11/2007 | Hully et al. |
| 2008/0131556 A1 | 6/2008 | De Simone et al. |
| 2010/0035232 A1 | 2/2010 | Ecker et al. |
| 2010/0129816 A1 | 5/2010 | Savelkoul et al. |
| 2010/0172874 A1 | 7/2010 | Turnbaugh et al. |
| 2011/0027219 A1 | 2/2011 | Tarcic et al. |
| 2011/0177976 A1 | 7/2011 | Gordon et al. |
| 2012/0045771 A1 | 2/2012 | Beier et al. |
| 2012/0129794 A1 | 5/2012 | Dowd et al. |
| 2012/0149584 A1 | 6/2012 | Olle et al. |
| 2012/0189621 A1 | 7/2012 | Dean et al. |
| 2012/0252775 A1 | 10/2012 | Finegold |
| 2013/0017999 A1 | 1/2013 | Fremont et al. |
| 2013/0045874 A1 | 2/2013 | Ehrlich |
| 2013/0108598 A1 | 5/2013 | Oresic et al. |
| 2013/0184302 A1 | 7/2013 | Bortey et al. |
| 2014/0093478 A1 | 4/2014 | Turnbaugh et al. |
| 2014/0136120 A1 | 5/2014 | Colwell et al. |
| 2014/0179726 A1 | 6/2014 | Bajaj et al. |
| 2014/0199281 A1 | 7/2014 | Henn et al. |
| 2014/0242080 A1 | 8/2014 | Jaeger et al. |
| 2014/0315929 A1 | 10/2014 | Chiosis |
| 2014/0341853 A1 | 11/2014 | Hovanky |
| 2014/0363399 A1 | 12/2014 | Jones et al. |
| 2014/0377270 A1 | 12/2014 | Moore et al. |
| 2015/0050245 A1 | 2/2015 | Herman et al. |
| 2015/0056206 A1 | 2/2015 | Zhou |
| 2015/0213193 A1 | 7/2015 | Apte et al. |
| 2015/0337349 A1 | 11/2015 | Kuczynski et al. |
| 2015/0374761 A1 | 12/2015 | Sadowsky et al. |
| 2016/0017058 A1 | 1/2016 | Kim et al. |
| 2016/0032363 A1 | 2/2016 | Stintzi et al. |
| 2016/0040216 A1 | 2/2016 | Akins et al. |
| 2016/0110515 A1 | 4/2016 | Apte et al. |
| 2016/0138089 A1 | 5/2016 | Harris et al. |
| 2017/0100329 A1 | 4/2017 | Kovarik et al. |
| 2017/0270268 A1 | 9/2017 | Apte et al. |

FOREIGN PATENT DOCUMENTS

| | | |
|---|---|---|
| EP | 2994756 | 3/2016 |
| WO | 050513 | 4/2012 |
| WO | 2014/107221 A1 | 7/2014 |
| WO | 121298 | 8/2014 |
| WO | 138999 | 9/2014 |
| WO | 144092 | 9/2014 |
| WO | 145958 | 9/2014 |
| WO | 013214 | 1/2015 |
| WO | 085326 | 6/2015 |
| WO | 095241 | 6/2015 |
| WO | 103165 | 7/2015 |
| WO | 112352 | 7/2015 |
| WO | 170979 | 11/2015 |
| WO | 2015/095241 A4 | 12/2015 |
| WO | 138337 | 9/2016 |
| WO | 172643 | 10/2016 |
| WO | 044902 | 3/2017 |

OTHER PUBLICATIONS

Avila, Maria et al., The Oral Microbiota: Living with a Permanent Guest, DNA and Cell Biology, Nov. 8, 2009, vol. 28, No. 8.
Carroll et al. "Alterations in composition and diversity of the intestinal microbiota in patients with diarrhea—predominant irritable bowel syndrome," Feb. 20, 2012 (Feb. 29, 2012), vol. 24, pp. 1-19 [Original pp. 5215-5230] entire document.
Cho et al. "The Human Microbiome: at the Interface of Health and Disease," Nature Reviews Genetics, Apr. 1, 2012 (Apr. 1, 2012), vol. 13, pp. 260-270.
Dewhirst, Floyd et al., The Human Oral Microbiome, Journal of Bacteriology, Oct. 2010, vol. 192, No. 19, pp. 5002-5017.
Evans, Morgan, Prosthetic valve endocarditis due to *Neisseria elongata* subsp. elongata in a patient with Klinefelter's syndrome, Journal of Medical Microbiology, Jun. 1, 2007, vol. 56, No. 6, pp. 860-862.
Greenblum et al. "Metagenomic Systems Biology of the Human Gut Microbiome Reveals Topological Shifts Associated with Obesity and Inflammatory Bowel Disease," Proceeding of the National Academy of Sciences, Dec. 19, 2011 (Dec. 19, 2011), vol. 109, pp. 594.
Kanehisa et al. "KEGG: Kyoto encyclopedia of genes and genomes," Nucleic Acids Research, Jan. 1, 2000 (Jan. 1, 2000), vol. 28, No. 1, pp. 27-30.
Mak et al. "MetaboLyzer: A Novel Statistical Workflow for Analyzing Post Processed LC/MS Metabolomics Data," Anal Chem, Jan. 7, 2014 (Jan. 7, 2014), vol. 86, pp. 506-513.
Morgan et al. "Dysfunction of the intestinal microbiome in inflammatory bowel disease and treatment," Genome Biol. Apr. 16, 2012 (Apr. 16, 2012), vol. 13(9):R79, pp. 1-18. entire document.
Mutlu et al. "A Compositional Look at the Human Gastrointestinal Microbiome and Immune Activation Parameters in HIV Infected Subjects," PLoS Pathogens, Feb. 20, 2014 (Feb. 20, 2014), vol. 10, pp. 1-18.
Nakayama et al. "Aberrant Structures of Fecal Bacterial Community in Allergic Infants Profiled by 16S rRNA Gene Pyrosequencing," FEMS Immunology & Medical Microbiology, Dec. 1, 2011 (Dec. 1, 2011), vol. 63, pp. 397-406.
Ponnusamy et al. "Microbial community and metabolomic comparison of irritable bowel syndrome faeces," Feb. 17, 2011 (Feb. 17, 2011), vol. 60, pp. 817-827. entire document.
International Application No. PCT/US2015/056767, International Preliminary Report on Patentability dated May 4, 2017, 9 pages.
International Application No. PCT/US2015/056767, International Search Report and Written Opinion dated Jan. 11, 2016, 10 pages.
International Application No. PCT/US2017/062720, International Search Report and Written Opinion Received dated Jan. 30, 2018, 8 pages.
U.S. Appl. No. 14/919,614, Non-Final Office Action dated Jul. 14, 2016, 10 pages.
U.S. Appl. No. 14/919,614, Notice of Allowance dated May 19, 2017, 10 pages.
U.S. Appl. No. 15/606,743, Non Final Office Action dated Dec. 19, 2017, 10 pages.
U.S. Appl. No. 15/606,743, Notice of Allowance dated Sep. 20, 2018, 5 pages.
U.S. Appl. No. 15/621,152, "Notice of Allowance," dated Mar. 8, 2019, 7 pages.
U.S. Appl. No. 15/621,144, "Notice of Allowance," dated Mar. 8, 2019, 7 pages.
U.S. Appl. No. 15/606,943, "Notice of Allowance," dated Mar. 8, 2019, 5 pages.
U.S. Appl. No. 15/606,824, "Notice of Allowance," dated Mar. 26, 2019, 6 pages.
U.S. Appl. No. 15/606,975, "Notice of Allowance," dated Apr. 3, 2019, 5 pages.

METHOD AND SYSTEM FOR CHARACTERIZING A HEADACHE-RELATED CONDITION

CROSS-REFERENCE TO RELATED APPLICATIONS

This application is a continuation-in-part of U.S. application Ser. No. 15/606,743, filed 26 May 2017, which is a continuation of U.S. application Ser. No. 14/919,614, filed 21 Oct. 2015, which claims the benefit of U.S. Provisional Application Ser. No. 62/066,369 filed 21 Oct. 2014, U.S. Provisional Application Ser. No. 62/087,551 filed 4 Dec. 2014, U.S. Provisional Application Ser. No. 62/092,999 filed 17 Dec. 2014, U.S. Provisional Application Ser. No. 62/147,376 filed 14 Apr. 2015, U.S. Provisional Application Ser. No. 62/147,212 filed 14 Apr. 2015, U.S. Provisional Application Ser. No. 62/147,362 filed 14 Apr. 2015, U.S. Provisional Application Ser. No. 62/146,855 filed 13 Apr. 2015, and U.S. Provisional Application Ser. No. 62/206,654 filed 18 Aug. 2015, which are each incorporated in its entirety herein by this reference.

This application also claims the benefit of U.S. Provisional Application Ser. No. 62/424,717 filed 21 Nov. 2016, which is herein incorporated in its entirety by this reference.

TECHNICAL FIELD

This invention relates generally to the field of microbiology and more specifically to a new and useful method and system for characterizing migraine in the field of microbiology.

BACKGROUND

A microbiome is an ecological community of commensal, symbiotic, and pathogenic microorganisms that are associated with an organism. The human microbiome includes over 10 times more microbial cells than human cells, but characterization of the human microbiome is still in nascent stages due to limitations in sample processing techniques, genetic analysis techniques, and resources for processing large amounts of data. Nonetheless, the microbiome is suspected to play at least a partial role in a number of health/disease-related states (e.g., preparation for childbirth, diabetes, auto-immune disorders, gastrointestinal disorders, rheumatoid disorders, neurological disorders, etc.). Given the profound implications of the microbiome in affecting a subject's health, efforts related to the characterization of the microbiome, the generation of insights from the characterization, and the generation of therapeutics configured to rectify states of dysbiosis should be pursued. Current methods and systems for analyzing the microbiomes of humans and providing therapeutic measures based on gained insights have, however, left many questions unanswered. In particular, methods for characterizing certain health conditions and therapies (e.g., probiotic therapies) tailored to specific subjects based upon microbiome composition and/or functional features have not been viable due to limitations in current technologies.

As such, there is a need in the field of microbiology for a new and useful method and system for characterizing health conditions in an individualized and population-wide manner. This invention creates such a new and useful method and system.

DESCRIPTION OF THE EMBODIMENTS

The following description of the embodiments of the invention is not intended to limit the invention to these embodiments, but rather to enable any person skilled in the art to make and use this invention.

1. Overview.

Figure 1A:
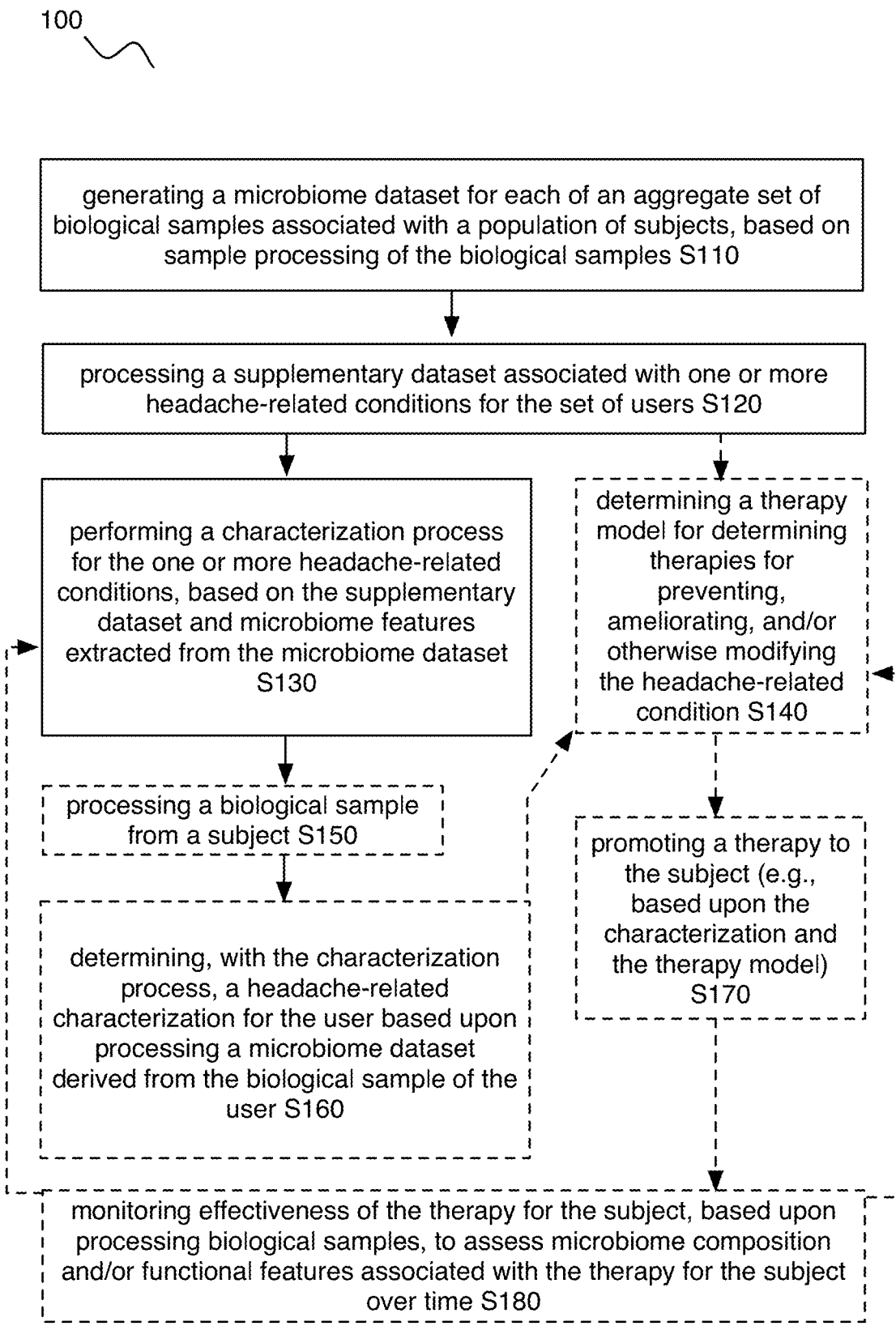
FIGS. 1A-1B is a flowchart representation of variations of an embodiment of a method.
Figure 1B:
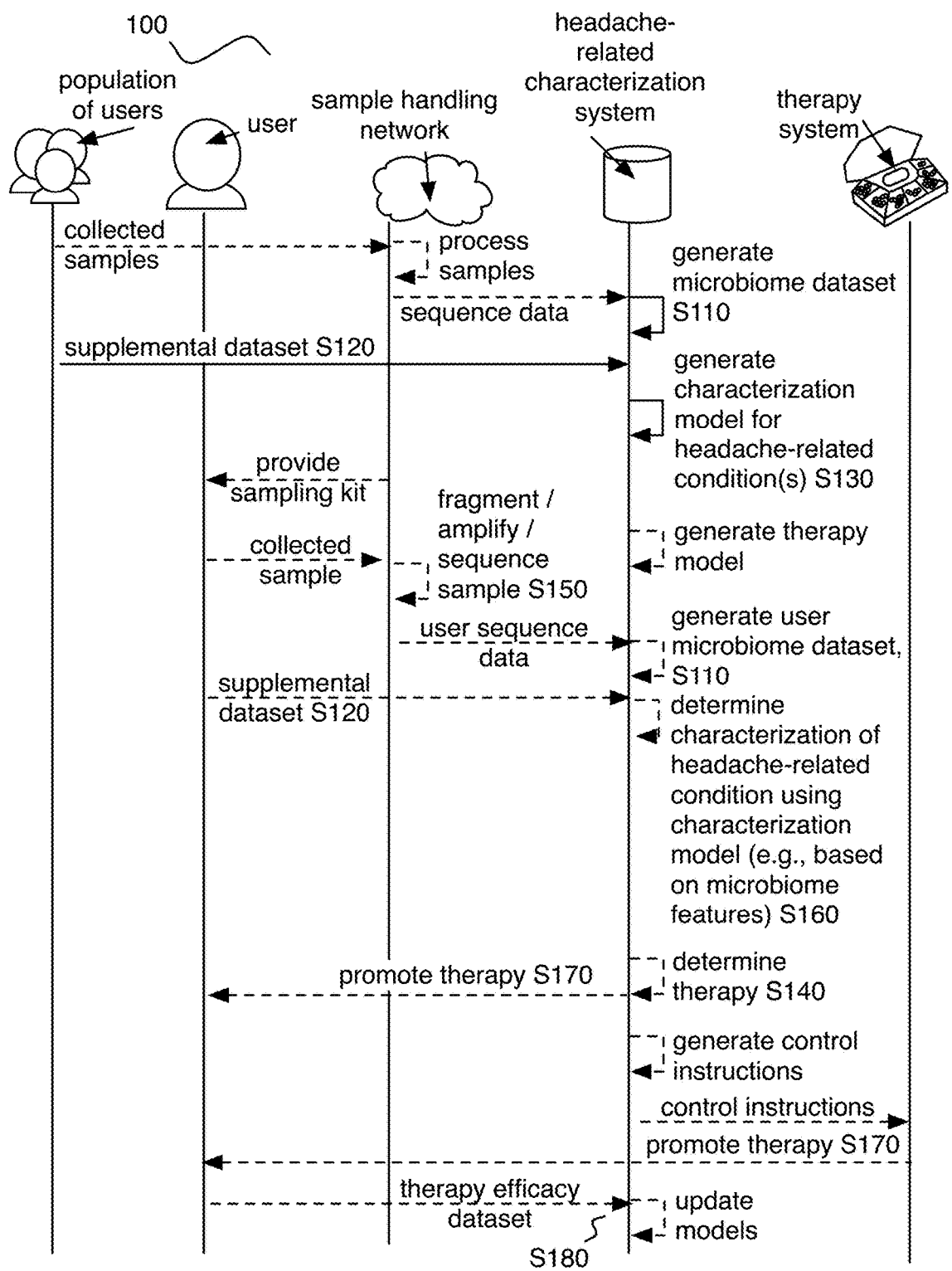

As shown in FIGS. 1A-1B, embodiments of a method 100 for characterizing a headache-related condition for a user can include one or more of: generating a microbiome dataset (e.g., microorganism sequence dataset, microbiome composition diversity dataset, microbiome functional diversity dataset, etc.) for each of an aggregate set of biological samples associated with a population of subjects, based on sample processing of the biological samples S110; processing a supplementary dataset associated with (e.g., informative of; describing; indicative of; etc.) one or more headache-related conditions for the set of users S120; and performing a characterization process for the one or more headache-related conditions, based on the supplementary dataset and microbiome features (e.g., microbiome composition diversity features; microbiome functional diversity features; etc.) extracted from the microbiome dataset S130. Embodiments of the method 100 can additionally or alternatively include one or more of: determining a therapy model for determining therapies for preventing, ameliorating, and/or otherwise modifying one or more headache-related conditions S140; processing one or more biological samples from a user (e.g., subject) S150; determining, with the characterization process, a headache-related characterization for the user based upon processing a microbiome dataset (e.g., user microorganism sequence dataset, microbiome composition dataset, microbiome functional diversity dataset, etc.) derived from the biological sample of the user S160; promoting a therapy for the headache-related condition to the user (e.g., based upon the headache-related characterization and/or a therapy model) S170; monitoring effectiveness of the therapy for the user, based upon processing biological samples, to assess microbiome composition and/or functional features associated with the therapy for the user over time S180; and/or any other suitable operations.

Embodiments of the method 100 and/or system 200 can function to characterize (e.g., assess, evaluate, diagnose, etc.) and/or treat users in relation to one or more headache-related conditions, based on at least one of user microbiome composition, microbiome function, and/or other suitable microbiome-related aspects. Additionally or alternatively, embodiments can function to determining headache-related characterizations and/or promote associated therapies in relation to specific physiological sites (e.g., gut, healthy gut, skin, nose, mouth, genitals, other suitable physiological sites, other sample collection sites, etc.). Additionally or alternatively, embodiments can perform any suitable functionality described herein. Additionally or alternatively, embodiments can function to generate models (e.g., headache-related characterization models; therapy models; etc.) that can be used to characterize and/or diagnose subjects according to at least one of their microbiome composition and functional features (e.g., as a clinical diagnostic, as a companion diagnostic, etc.), and/or provide therapeutic measures (e.g., probiotic-based therapeutic measures, phage-based therapeutic measures, small-molecule-based therapeutic measures, clinical measures, etc.) to subjects in relation to one or more headache-related conditions. As such, data from the population of subjects can be used to characterize subjects according to their microbiome composition and/or functional features, indicate states of health and areas of improvement based upon the characterization(s), and promote one or more therapies that can modulate the composition of a subject's microbiome toward one or more of a set of desired equilibrium states. Variations of the method 100 can further facilitate monitoring and/or adjusting of therapies provided to a subject, for instance, through reception, processing, and analysis of additional samples from a subject throughout the course of therapy. In specific examples, the method 100 can be used to promote targeted therapies to subjects suffering from migraine.

Embodiments of the method 100 and/or system 200 can preferably generate and promote characterizations and/or therapies for headache-related conditions, which can include any one or more of headache-related: symptoms, causes (e.g., triggers), diseases, disorders, and/or any other suitable aspects associated with headache-related conditions. Headache-related conditions can include any one or more of: a migraine condition (e.g., migraine without aura, migraine with aura, migraine without headache, migraine with brainstem aura, hemiplegic migraine, retinal migraine, chronic migraine, etc.); tension-type headaches; cluster headaches; medication-overuse headaches; primary headaches; secondary headaches; acute headaches; frequent headaches; severe headaches; throbbing headaches; and/or any other suitable headache-related conditions. Migraine conditions and/or other suitable headache-related conditions can include symptoms including: bodily pain (e.g., face, neck, dull pain, tenderness, etc.); dizziness; lightheadedness; malaise; sensory sensitivity (e.g., to light, aura, sound, etc.); gastrointestinal symptoms (e.g., nausea, vomiting, etc.); visual symptoms (e.g., distorted vision, light flashes); congestion; irritability; and/or any other suitable symptoms.

Embodiments of the method 100 and/or system 200 can be implemented for a single subject for whom microbiome characterization and/or microbiome modulation with therapeutics is of interest, and can additionally or alternatively be implemented for a population of subjects (e.g., including the subject, excluding the subject), where the population of subjects can include patients dissimilar to and/or similar to the subject (e.g., in health condition, in dietary needs, in demographic features, etc.). Thus, information derived from the population of subjects can be used to provide additional insight into connections between behaviors of a subject and effects on the subject's microbiome, due to aggregation of data from a population of subjects. In a variation, an aggregate set of biological samples is preferably received from a wide variety of subjects, collectively including subjects of one or more of: different demographics (e.g., genders, ages, marital statuses, ethnicities, nationalities, socioeconomic statuses, sexual orientations, etc.), different health conditions (e.g., health and disease states), different living situations (e.g., living alone, living with pets, living with a significant other, living with children, etc.), different dietary habits (e.g., omnivorous, vegetarian, vegan, sugar consumption, acid consumption, caffeine consumption, etc.), different behavioral tendencies (e.g., levels of physical activity, drug use, alcohol use, etc.), different levels of mobility (e.g., related to distance traveled within a given time period), and/or any other suitable trait that has an effect on microbiome composition and/or functional features. As such, as the number of subjects increases, the predictive power of processes implemented in portions of the method 100 increases, in relation to characterizing a variety of subjects based upon their microbiomes. However, the method 100 can involve generation of characterization and therapies derived from biological sample data from any other suitable group of subjects.

Data described herein (e.g., sequence data, microbiome composition features, microbiome functional features, headache-related characterizations, therapy determinations, etc.) can be associated with any suitable temporal indicators (e.g., seconds, minutes, hours, days, weeks, etc.) including one or more: temporal indicators indicating when the data was collected (e.g., temporal indicators indicating when a sample was collected; etc.), determined, transmitted, received, and/or otherwise processed; temporal indicators providing context to content described by the data (e.g., temporal indicators associated with headache-related characterizations, such as where the headache-related characterization describes the headache-related conditions and/or user microbiome status a particular time; etc.); changes in temporal indicators (e.g., changes in headache-related characterizations over time, such as in response to consumed therapies; latency between sample collection and sample analysis; etc.); and/or any other suitable indicators related to time.

Additionally or alternatively, parameters, metrics, inputs, outputs, and/or other suitable data can be associated with value types including: scores (e.g., microbiome diversity scores; risk scores for headache-related conditions; microbiome composition diversity scores; microbiome functional diversity scores; etc.), binary values (e.g., presence or absence of a microbiome feature; presence or absence of a headache-related condition; etc.), classifications (e.g., headache-related condition classifications; behavioral classifications; demographic classifications; etc.), confidence levels (e.g., associated with microorganism sequence datasets; with microbiome diversity scores; with other headache-related characterizations; etc.), values along a spectrum, and/or any other suitable types of values. Any suitable types of data described herein can be used as inputs (e.g., for different models described herein), generated as outputs (e.g., of different models), and/or manipulated in any suitable manner for any suitable components associated with the method 100 and/or system 200.

One or more instances and/or portions of the method 100 and/or processes described herein can be performed asynchronously (e.g., sequentially), concurrently (e.g., multiplex sample processing, such as multiplex amplification of microorganism nucleic acid fragments corresponding to target sequences associated with headache-related conditions; computationally determining microbiome datasets, microbiome features, and/or headache-related conditions in parallel for a plurality of users, such as concurrently on different threads for parallel computing to improve system processing ability; etc.), in temporal relation to a trigger event (e.g., performance of a portion of the method 100), and/or in any other suitable order at any suitable time and frequency by and/or using one or more instances of the system 200, components, and/or entities described herein. For example, the method 100 can include generating a microorganism sequence dataset based on processing microorganism nucleic acids of a biological sample with a bridge amplification substrate of a next generation sequencing platform of a sample handling system, and determining microbiome composition diversity features and microbiome functional diversity features at computing devices operable to communicate with the next generation sequencing platform.

Figure 2:
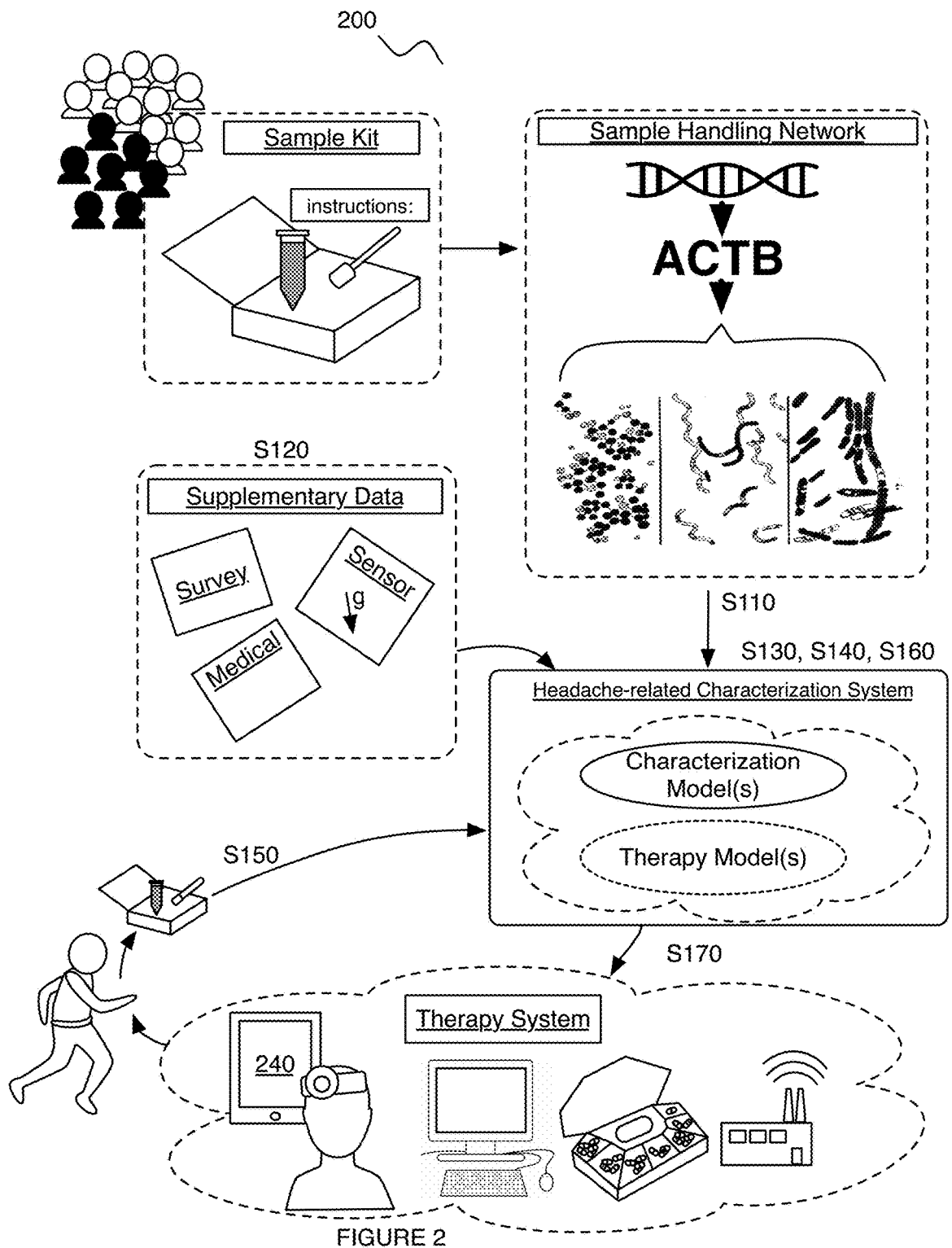
FIG. 2 depicts embodiments of a method and system.

As shown in FIG. 2, embodiments of the system 200 can include any one or more of: a handling system (e.g., a sample handling system, etc.) operable to collect biological samples (e.g., collected by users and included in containers including pre-processing reagents; etc.) from one or more users (e.g., a human subject, patient, animal subject, environmental ecosystem, care provider, etc.), the handling system including a sequencing platform (e.g., next-generation sequencing platform) operable to determine a microorganism sequence dataset for the one or more users from the biological samples; a headache-related characterization system operable to: determine user microbiome features (e.g., microbiome composition features; microbiome functional features; diversity features; relative abundance ranges; etc.) based on the microorganism sequence dataset, and determine headache-related characterizations based on the user microbiome features; and/or a treatment system operable to promote a therapy for one or more headache-related conditions based on the headache-related characterization. However, the method 100 and/or system 200 can be configured in any suitable manner.

2. Benefits.

Microbiome analysis can enable accurate and efficient characterization and/or therapy provision for headache-related conditions caused by and/or otherwise associated with microorganisms. The technology can overcome several challenges faced by conventional approaches in characterizing and/or promoting therapies for a condition. First, conventional approaches can require patients to visit one or more care providers to receive a characterization and/or a therapy recommendation for a headache-related condition, which can amount to inefficiencies and health-risks associated with the amount of time elapsed before diagnosis and/or treatment. Second, conventional genetic sequencing and analysis technologies for human genome sequencing can be incompatible and/or inefficient when applied to the microbiome (e.g., where the human microbiome can include over 10 times more microbial cells than human cells; where optimal sample processing techniques can differ, such as for reducing amplification bias; where different approaches to headache-related characterizations can be employed; where the types of conditions and correlations can differ; where sequence reference databases can differ; where the microbiome can vary across different body regions of the user; etc.). Third, the onset of sequencing technologies (e.g., next-generation sequencing) has given rise to technological issues (e.g., data processing and analysis issues for the plethora of generated sequence data; issues with processing a plurality of biological samples in a multiplex manner; information display issues; therapy prediction issues; therapy provision issues, etc.) that would not exist but for the unprecedented advances in speed and data generation associated with sequencing genetic material. Specific examples of the method 100 and/or system 200 can confer technologically-rooted solutions to at least the challenges described above.

First, the technology can confer improvements in computer-related technology (e.g., modeling associated with characterizing and/or promoting therapies for headache-related conditions; improving computational efficiency in storing, retrieving, and/or processing microorganism-related data for headache-related conditions; computational processing associated with biological sample processing; etc.) by facilitating computer performance of functions not previously performable. For example, the technology can computationally generate headache-related characterizations and/or recommended therapies associated with microbiome analysis based on techniques (e.g., leveraging microorganism taxonomic databases, etc.) that are recently viable due to advances in sample processing techniques and sequencing technology.

Second, the technology can confer improvements in processing speed, headache-related characterization accuracy, microbiome-related therapy determination and promotion, and/or other suitable aspects in relation to headache-related conditions. For example, the technology can generate and apply feature-selection rules (e.g., microbiome diversity feature-selection rules for composition, function, etc.) to select an optimized subset of features (e.g., microbiome composition diversity features such as reference relative abundance features indicative of healthy ranges of taxonomic groups associated with headache-related conditions; user relative abundance features that can be compared to reference relative abundance features correlated with headache-related conditions and/or therapy responses; etc.) out of a vast potential pool of features (e.g., extractable from the plethora of microbiome data such as sequence data) for generating and/or applying characterization models and/or therapy models. The potential size of microbiomes (e.g., human microbiomes, animal microbiomes, etc.) can translate into a plethora of data, giving rise to questions of how to process and analyze the vast array of data to generate actionable microbiome insights in relation to headache-related conditions. However, the feature-selection rules and/or other suitable computer-implementable rules can enable one or more of: shorter generation and execution times (e.g., for generating and/or applying models; for determining headache-related characterizations and/or associated therapies; etc.); optimized sample processing techniques (e.g., improving transformation of microorganism nucleic acids from biological samples through using primer types, other biomolecules, and/or other sample processing components identified through computational analysis of taxonomic groups, sequences, and/or other suitable data associated with headache-related conditions, such as while optimizing for improving specificity, reducing amplification bias, and/or other suitable parameters; etc.); model simplification facilitating efficient interpretation of results; reduction in overfitting; network effects associated with generating, storing, and applying microbiome characterizations for a plurality of users over time in relation to headache-related conditions (e.g., through collecting and processing an increasing amount of microbiome-related data associated with an increasing number of users to improve predictive power of the headache-related characterizations and/or therapy determinations; etc.), improvements in data storage and retrieval (e.g., storing specific models, microorganism sequences, features, headache-related characterizations, and/or other suitable data in association with a user and/or set of users to improve delivery of personalized characterizations and/or treatments for the headache-related conditions, etc.), and/or other suitable improvements to technological areas.

Third, the technology can transform entities (e.g., users, biological samples, treatment systems including medical devices, etc.) into different states or things. For example, the technology can transform a biological sample into components able to be sequenced and analyzed for characterizing users in relation to headache-related conditions. In another example, the technology can identify therapies to promote to a patient to modify a microbiome composition (e.g., composition diversity), microbiome function (e.g., functional diversity) and/or other microbiome-related aspects to prevent and/or ameliorate one or more headache-related conditions, thereby transforming the microbiome and/or health of the patient. In another example, the technology can control treatment systems to promote therapies (e.g., by generating control instructions for the treatment system to execute), thereby transforming the treatment system.

Fourth, the technology can amount to an inventive distribution of functionality across a network including a sample handling system, a headache-related characterization system, and a plurality of users, where the sample handling system can handle substantially concurrent processing of biological samples (e.g., in a multiplex manner) from the plurality of users, which can be leveraged by the headache-related characterization system in generating personalized characterizations and/or therapies (e.g., customized to the user's microbiome such as in relation to the user's dietary behavior, probiotics-associated behavior, medical history, demographics, other behaviors, preferences, etc.) for headache-related conditions.

Fifth, the technology can improve the technical fields of at least microbiome-related digital medicine, digital medicine generally, genetic sequencing, modeling (e.g., of headache-related conditions associated with microbiomes; etc.) and/or other relevant fields. Sixth, the technology can leverage specialized computing devices (e.g., devices associated with the sample handling system, such as next-generation sequencing platforms; headache-related characterization systems; treatment systems; etc.) in determining and processing microbiome datasets in relation to headache-related characterization and/or therapy provision. The technology can, however, provide any other suitable benefit(s) in the context of using non-generalized computer systems for headache-related characterization and/or microbiome modulation.

3.1 Method—Generating a Microbiome Dataset.

Block S110 recites: generating a microbiome dataset (e.g., microorganism sequence dataset, microbiome composition diversity dataset, microbiome functional diversity dataset, etc.) for each of an aggregate set of biological samples associated with a population of users (e.g., subjects), based on sample processing of the biological samples. Block S110 functions to process each of an aggregate set of biological samples (e.g., associated with a population of subjects, a subpopulation of subjects, a subgroup of subjects sharing a demographic characteristic and/or other suitable characteristics, etc.), in order to determine compositional, functional, pharmacogenomics, and/or other suitable aspects associated with the microbiomes of the users, such as in relation to one or more headache-related conditions. Compositional and/or functional aspects can include one or more of aspects at the microorganism level, including parameters related to distribution of microorganisms across different groups of kingdoms, phyla, classes, orders, families, genera, species, subspecies, strains, and/or any other suitable infraspecies taxon (e.g., as measured in total abundance of each group, relative abundance of each group, total number of groups represented, etc.). Compositional and/or functional aspects can also be represented in terms of operational taxonomic units (OTUs). Compositional and/or functional aspects can additionally or alternatively include compositional aspects at the genetic level (e.g., regions determined by multilocus sequence typing, 16S sequences, 18S sequences, ITS sequences, other genetic markers, other phylogenetic markers, etc.). Compositional and functional aspects can include the presence or absence or the quantity of genes associated with specific functions (e.g. enzyme activities, transport functions, immune activities, etc.). Outputs of Block S110 can thus be used to provide features of interest for the characterization process of Block S130 and/or other suitable portions of the method 100 (e.g., where Block S110 can lead to outputs of microbiome composition datasets, microbiome functional datasets, and/or other suitable microbiome datasets from which microbiome features can be extracted, etc.), where the features can be microorganism-based (e.g., presence of a genus of bacteria), genetic-based (e.g., based upon representation of specific genetic regions and/or sequences) and/or functional-based (e.g., presence of a specific catalytic activity).

In one variation, Block S110 can include assessment and/or processing based upon phylogenetic markers derived from bacteria and/or archaea in relation to gene families associated with one or more of: ribosomal protein S2, ribosomal protein S3, ribosomal protein S5, ribosomal protein S7, ribosomal protein S8, ribosomal protein S9, ribosomal protein S10, ribosomal protein S11, ribosomal protein S12/S23, ribosomal protein S13, ribosomal protein S15P/S13e, ribosomal protein S17, ribosomal protein S19, ribosomal protein L1, ribosomal protein L2, ribosomal protein L3, ribosomal protein L4/L1e, ribosomal protein L5, ribosomal protein L6, ribosomal protein L10, ribosomal protein L11, ribosomal protein L14b/L23e, ribosomal protein L15, ribosomal protein L16/L10E, ribosomal protein L18P/L5E, ribosomal protein L22, ribosomal protein L24, ribosomal protein L25/L23, ribosomal protein L29, translation elongation factor EF-2, translation initiation factor IF-2, metalloendopeptidase, ffh signal recognition particle protein, phenylalanyl-tRNA synthetase beta subunit, phenylalanyl-tRNA synthetase alpha subunit, tRNA pseudouridine synthase B, Porphobilinogen deaminase, ribosomal protein L13, phosphoribosylformylglycinamidine cyclo-ligase, and ribonuclease HII. Additionally or alternatively, markers can include target sequences (e.g., sequences associated with a microorganism taxonomic group; sequences associated with functional aspects; sequences correlated with headache-related conditions; sequences indicative of user responsiveness to different therapies; sequences that are invariant across a population and/or any suitable set of subjects, such as to facilitate multiplex amplification using a primer type sharing a primer sequence; conserved sequences; sequences including mutations, polymorphisms; nucleotide sequences; amino acid sequences; etc.), proteins (e.g., serum proteins, antibodies, etc.), peptides, carbohydrates, lipids, other nucleic acids, whole cells, metabolites, natural products, genetic predisposition biomarkers, diagnostic biomarkers, prognostic biomarkers, predictive biomarkers, other molecular biomarkers, gene expression markers, imaging biomarkers, and/or other suitable markers. However, markers can include any other suitable marker(s) associated with microbiome composition, microbiome functionality, and/or headache-related conditions.

Characterizing the microbiome composition and/or functional aspects for each of the aggregate set of biological samples thus preferably includes a combination of sample processing techniques (e.g., wet laboratory techniques) and computational techniques (e.g., utilizing tools of bioinformatics) to quantitatively and/or qualitatively characterize the microbiome and functional aspects associated with each biological sample from a subject or population of subjects.

In variations, sample processing in Block S110 can include any one or more of: lysing a biological sample, disrupting membranes in cells of a biological sample, separation of undesired elements (e.g., RNA, proteins) from the biological sample, purification of nucleic acids (e.g., DNA) in a biological sample, amplification of nucleic acids from the biological sample, further purification of amplified nucleic acids of the biological sample, and sequencing of amplified nucleic acids of the biological sample. In an example, Block S110 can include: collecting biological samples from a set of users (e.g., biological samples collected by the user with a sampling kit including a sample container, etc.), where the biological samples include microorganism nucleic acids associated with the headache-related condition (e.g., microorganism nucleic acids including target sequences correlated with a headache-related condition; etc.). In another example, Block S110 can include providing a set of sampling kits to a set of users, each sampling kit of the set of sampling kits including a sample container (e.g., including pre-processing reagents, such as lysing reagents; etc.) operable to receive a biological sample from a user of the set of users.

In variations, lysing a biological sample and/or disrupting membranes in cells of a biological sample preferably includes physical methods (e.g., bead beating, nitrogen decompression, homogenization, sonication), which omit certain reagents that produce bias in representation of certain bacterial groups upon sequencing. Additionally or alternatively, lysing or disrupting in Block S110 can involve chemical methods (e.g., using a detergent, using a solvent, using a surfactant, etc.). Additionally or alternatively, lysing or disrupting in Block S110 can involve biological methods. In variations, separation of undesired elements can include removal of RNA using RNases and/or removal of proteins using proteases. In variations, purification of nucleic acids can include one or more of: precipitation of nucleic acids from the biological samples (e.g., using alcohol-based precipitation methods), liquid-liquid based purification techniques (e.g., phenol-chloroform extraction), chromatography-based purification techniques (e.g., column adsorption), purification techniques involving use of binding moiety-bound particles (e.g., magnetic beads, buoyant beads, beads with size distributions, ultrasonically responsive beads, etc.) configured to bind nucleic acids and configured to release nucleic acids in the presence of an elution environment (e.g., having an elution solution, providing a pH shift, providing a temperature shift, etc.), and any other suitable purification techniques.

In variations, amplification of purified nucleic acids preferably includes one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably selected to prevent or minimize amplification bias, as well as configured to amplify nucleic acid regions/sequences (e.g., of the 16S region, the 18S region, the ITS region, etc.) that are informative taxonomically, phylogenetically, for diagnostics, for formulations (e.g., for probiotic formulations), and/or for any other suitable purpose. Thus, universal primers (e.g., a F27-R338 primer set for 16S RNA, a F515-R806 primer set for 16S RNA, etc.) configured to avoid amplification bias can be used in amplification. Additionally or alternatively include incorporated barcode sequences specific to biological samples, to users, to headache-related conditions, to taxa, to target sequences, and/or to any other suitable components, which can facilitate a post-sequencing identification process (e.g., for mapping sequence reads to microbiome composition and/or microbiome function aspects; etc.). Primers used in variations of Block S110 can additionally or alternatively include adaptor regions configured to cooperate with sequencing techniques involving complementary adaptors (e.g., Illumina Sequencing). Additionally or alternatively, Block S110 can implement any other step configured to facilitate processing (e.g., using a Nextera kit). In a specific example, performing amplification and/or sample processing operations can be in a multiplex manner (e.g., for a single biological sample, for a plurality of biological samples across multiple users; etc.).

In variations, sequencing of purified nucleic acids can include methods involving targeted amplicon sequencing and/or metagenomic sequencing, implementing techniques including one or more of: sequencing-by-synthesis techniques (e.g., Illumina sequencing), capillary sequencing techniques (e.g., Sanger sequencing), pyrosequencing techniques, and nanopore sequencing techniques (e.g., using an Oxford Nanopore technique).

In a specific example, amplification and sequencing of nucleic acids from biological samples of the set of biological samples includes: solid-phase PCR involving bridge amplification of DNA fragments of the biological samples on a substrate with oligo adapters, where amplification involves primers having a forward index sequence (e.g., corresponding to an Illumina forward index for MiSeq/NextSeq/HiSeq platforms), a forward barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, a sequence for targeting a specific target region (e.g., 16S region, 18S region, ITS region), a reverse index sequence (e.g., corresponding to an Illumina reverse index for MiSeq/HiSeq platforms), and a reverse barcode sequence. In the specific example, sequencing includes Illumina sequencing (e.g., with a HiSeq platform, with a MiSeq platform, with a NextSeq platform, etc.) using a sequencing-by-synthesis technique.

In variations, primers (e.g., of a primer type corresponding to a primer sequence; etc.) used in Block S110 and/or other suitable portions of the method 100 can include primers associated with protein genes (e.g., coding for conserved protein gene sequences across a plurality of taxa, such as to enable multiplex amplification for a plurality of targets and/or taxa; etc.). Primers can additionally or alternatively be associated with headache-related conditions, microbiome composition features (e.g., identified primers compatible with a genetic target corresponding to microbiome composition features associated with a group of taxa correlated with a headache-related condition; genetic sequences from which relative abundance features are derived etc.), functional diversity features, supplementary features, and/or other suitable features and/or data. Primers (and/or other suitable molecules, markers, and/or biological material described herein) can possess any suitable size (e.g., sequence length, number of base pairs, conserved sequence length, variable region length, etc.). Additionally or alternatively, any suitable number of primers can be used in sample processing for performing characterizations (e.g., headache-related characterizations; etc.), improving sample processing (e.g., through reducing amplification bias, etc.), and/or for any suitable purposes. The primers can be associated with any suitable number of targets, sequences, taxa, conditions, and/or other suitable aspects. Primers used in Block S110 and/or other suitable portions of the method 100 can be selected through processes described in Block S110 (e.g., primer selection based on parameters used in generating the taxonomic database) and/or any other suitable portions of the method 100. In an example, Block S110 can include: identifying a primer type for a microorganism nucleic acid sequence associated with the headache-related condition (e.g., a primer type for a primer operable to amplify microorganism nucleic acid sequences correlated with a headache-related condition; etc.); and generating the microorganism sequence dataset based on the primer type and the microorganism nucleic acids (e.g., using primers of the primer type for amplification of microorganism nucleic acids; and sequencing the amplified nucleic acids to generate the microorganism sequence dataset; etc.). In a specific example, Block S110 can include: fragmenting the microorganism nucleic acids; and performing multiplex amplification with the fragmented microorganism nucleic acids based on the fragmented microorganism nucleic acids and the identified primer type associated with the headache-related condition. Additionally or alternatively, primers (and/or processes associated with primers) can include and/or be analogous to that described in U.S. application Ser. No. 14/919,614, filed 21 Oct. 2015, which is herein incorporated in its entirety by this reference. However, identification and/or usage of primers can be configured in any suitable manner.

Some variations of sample processing can include further purification of amplified nucleic acids (e.g., PCR products) prior to sequencing, which functions to remove excess amplification elements (e.g., primers, dNTPs, enzymes, salts, etc.). In examples, additional purification can be facilitated using any one or more of: purification kits, buffers, alcohols, pH indicators, chaotropic salts, nucleic acid binding filters, centrifugation, and/or any other suitable purification technique.

In variations, computational processing in Block S110 can include any one or more of: identification of microbiome-derived sequences (e.g., as opposed to subject sequences and contaminants), alignment and mapping of microbiome-derived sequences (e.g., alignment of fragmented sequences using one or more of single-ended alignment, ungapped alignment, gapped alignment, pairing), and generating features derived from compositional and/or functional aspects of the microbiome associated with a biological sample.

Identification of microbiome-derived sequences can include mapping of sequence data from sample processing to a subject reference genome (e.g., provided by the Genome Reference Consortium), in order to remove subject genome-derived sequences. Unidentified sequences remaining after mapping of sequence data to the subject reference genome can then be further clustered into operational taxonomic units (OTUs) based upon sequence similarity and/or reference-based approaches (e.g., using VAMPS, using MG-RAST, using QIIME databases), aligned (e.g., using a genome hashing approach, using a Needleman-Wunsch algorithm, using a Smith-Waterman algorithm), and mapped to reference bacterial genomes (e.g., provided by the National Center for Biotechnology Information), using an alignment algorithm (e.g., Basic Local Alignment Search Tool, FPGA accelerated alignment tool, BWT-indexing with BWA, BWT-indexing with SOAP, BWT-indexing with Bowtie, etc.). Mapping of unidentified sequences can additionally or alternatively include mapping to reference archaeal genomes, viral genomes and/or eukaryotic genomes. Furthermore, mapping of taxons can be performed in relation to existing databases, and/or in relation to custom-generated databases.

Upon identification of represented groups of microorganisms of the microbiome associated with a biological sample, generating features derived from compositional and functional aspects of the microbiome associated with a biological sample can be performed. In one variation, generating features can include generating features based upon multilocus sequence typing (MSLT), in order to identify markers useful for characterization in subsequent blocks of the method 100. Additionally or alternatively, generated features can include generating features that describe the presence or absence of certain taxonomic groups of microorganisms, and/or ratios between exhibited taxonomic groups of microorganisms. Additionally or alternatively, generating features can include generating features describing one or more of: quantities of represented taxonomic groups, networks of represented taxonomic groups, correlations in representation of different taxonomic groups, interactions between different taxonomic groups, products produced by different taxonomic groups, interactions between products produced by different taxonomic groups, ratios between dead and alive microorganisms (e.g., for different represented taxonomic groups, based upon analysis of RNAs), phylogenetic distance (e.g., in terms of Kantorovich-Rubinstein distances, Wasserstein distances etc.), any other suitable taxonomic group-related feature(s), any other suitable genetic or functional aspect(s).

Additionally or alternatively, generating features can include generating features describing relative abundance of different microorganism groups, for instance, using a sparCC approach, using Genome Relative Abundance and Average size (GAAS) approach and/or using a Genome Relative Abundance using Mixture Model theory (GRAMMy) approach that uses sequence-similarity data to perform a maximum likelihood estimation of the relative abundance of one or more groups of microorganisms. Additionally or alternatively, generating features can include generating statistical measures of taxonomic variation, as derived from abundance metrics. Additionally or alternatively, generating features can include generating features derived from relative abundance factors (e.g., in relation to changes in abundance of a taxon, which affects abundance of other taxons). Additionally or alternatively, generating features can include generation of qualitative features describing presence of one or more taxonomic groups, in isolation and/or in combination. Additionally or alternatively, generating features can include generation of features related to genetic markers (e.g., representative 16S, 18S, and/or ITS sequences) characterizing microorganisms of the microbiome associated with a biological sample. Additionally or alternatively, generating features can include generation of features related to functional associations of specific genes and/or organisms having the specific genes. Additionally or alternatively, generating features can include generation of features related to pathogenicity of a taxon and/or products attributed to a taxon. Block S120 can, however, include generation of any other suitable feature(s) derived from sequencing and mapping of nucleic acids of a biological sample. For instance, the feature(s) can be combinatory (e.g. involving pairs, triplets), correlative (e.g., related to correlations between different features), and/or related to changes in features (i.e., temporal changes, changes across sample sites, etc., spatial changes, etc.). However, processing biological samples, generating a microbiome dataset, and/or other aspects associated with Block S110 can be performed in any suitable manner.

3.2 Method—Processing a Supplementary Dataset.

Block S120 recites: processing (e.g., receiving, collecting, transforming, etc.) a supplementary dataset associated with (e.g., informative of; describing; indicative of; etc.) one or more headache-related conditions for the set of users. Block S120 functions to acquire additional data associated with one or more subjects of the set of subjects, which can be used to train, validate, apply, and/or otherwise inform the headache-related characterization process (e.g., in Block S130). In Block S120, the supplementary dataset preferably includes survey-derived data, but can additionally or alternatively include any one or more of: contextual data derived from sensors, medical data (e.g., current and historical medical data; medical device-derived data; data associated with medical tests; etc.), and any other suitable type of data. In variations of Block S120 including reception of survey-derived data, the survey-derived data preferably provides physiological, demographic, and behavioral information in association with a subject. Physiological information can include information related to physiological features (e.g., height, weight, body mass index, body fat percent, body hair level, etc.). Demographic information can include information related to demographic features (e.g., gender, age, ethnicity, marital status, number of siblings, socioeconomic status, sexual orientation, etc.). Behavioral information can include information related to one or more of: health conditions (e.g., health and disease states), living situations (e.g., living alone, living with pets, living with a significant other, living with children, etc.), dietary habits (e.g., omnivorous, vegetarian, vegan, sugar consumption, acid consumption, etc.), behavioral tendencies (e.g., levels of physical activity, drug use, alcohol use, etc.), different levels of mobility (e.g., related to distance traveled within a given time period), different levels of sexual activity (e.g., related to numbers of partners and sexual orientation), and any other suitable behavioral information. Survey-derived data can include quantitative data and/or qualitative data that can be converted to quantitative data (e.g., using scales of severity, mapping of qualitative responses to quantified scores, etc.).

In facilitating reception of survey-derived data, Block S130 can include providing one or more surveys to a subject of the population of subjects, or to an entity associated with a subject of the population of subjects. Surveys can be provided in person (e.g., in coordination with sample provision and reception from a subject), electronically (e.g., during account setup by a subject, at an application executing at an electronic device of a subject, at a web application accessible through an internet connection, etc.), and/or in any other suitable manner.

Additionally or alternatively, portions of the supplementary dataset can be derived from sensors associated with the subject(s) (e.g., sensors of wearable computing devices, sensors of mobile devices, biometric sensors associated with the user, etc.). As such, Block S130 can include receiving one or more of: physical activity- or physical action-related data (e.g., accelerometer and gyroscope data from a mobile device or wearable electronic device of a subject), environmental data (e.g., temperature data, elevation data, climate data, light parameter data, etc.), patient nutrition or diet-related data (e.g., data from food establishment check-ins, data from spectrophotometric analysis, user-inputted data, nutrition data associated with probiotic and/or prebiotic food items, types of food consumed, amount of food consumed, diets, etc.), biometric data (e.g., data recorded through sensors within the patient's mobile computing device, data recorded through a wearable or other peripheral device in communication with the patient's mobile computing device), location data (e.g., using GPS elements), and any other suitable data. In variations, sensor data can include data sampled at one or more: optical sensors (e.g., image sensors, light sensors, etc.), audio sensors, temperature sensors, volatile compound sensors, weight sensors, humidity sensors, depth sensors, location sensors (GPS receivers; etc.), inertial sensors (e.g., accelerators, gyroscope, magnetometer, etc.), biometric sensors (e.g., heart rate sensors, fingerprint sensors, bio-impedance sensors, etc.), pressure sensors, flow sensors, power sensors (e.g., Hall effect sensors), and/or or any other suitable sensor.

Additionally or alternatively, portions of the supplementary dataset can be derived from medical record data and/or clinical data of the subject(s). As such, portions of the supplementary dataset can be derived from one or more electronic health records (EHRs) of the subject(s).

Additionally or alternatively, the supplementary dataset of Block S120 can include any other suitable diagnostic information (e.g., clinical diagnosis information), which can be combined with analyses derived from features to support characterization of subjects in subsequent blocks of the method 100. For instance, information derived from a colonoscopy, biopsy, blood test, diagnostic imaging, survey-related information, and any other suitable test can be used to supplement Additionally or alternatively, the supplementary dataset can include therapy-related data including one or more of: therapy regimens, types of therapies, recommended therapies, therapies used by the user, therapy adherence, etc. For example, the supplementary dataset can include user adherence (e.g., medication adherence, probiotic adherence, physical exercise adherence, dietary adherence, etc.) to a recommended therapy. However, processing supplementary datasets can be performed in any suitable manner.

3.3 Method—Performing a Characterization Process.

Block S130 recites: performing a characterization process for the one or more headache-related conditions, based on the supplementary dataset and microbiome features (e.g., microbiome composition diversity features; microbiome functional diversity features; etc.) extracted from the microbiome dataset. Block S130 can function to identify, extract, and/or otherwise process features and/or feature combinations that can be used to characterize subjects or groups based upon their microbiome composition features, functional features, and/or other suitable microbiome features (e.g., such as through the generation and application of a characterization model for determining headache-related characterizations, etc.). As such, the characterization process can be used as a diagnostic tool that can characterize a subject (e.g., in terms of behavioral traits, in terms of medical conditions, in terms of demographic traits, etc.) based upon their microbiome composition and/or functional features, in relation to one or more of their health condition states (e.g., headache-related condition states), behavioral traits, medical conditions, demographic traits, and/or any other suitable traits. Such characterization can then be used to suggest or provide personalized therapies by way of the therapy model of Block S140.

In performing the characterization process, Block S130 can use computational methods (e.g., statistical methods, machine learning methods, artificial intelligence methods, bioinformatics methods, etc.) to characterize a subject as exhibiting features characteristic of a group of subjects with a health condition.

In one variation, characterization can be based upon features derived from a statistical analysis (e.g., an analysis of probability distributions) of similarities and/or differences between a first group of subjects exhibiting a target state (e.g., a health condition state) and a second group of subjects not exhibiting the target state (e.g., a "normal" state). In implementing this variation, one or more of a Kolmogorov-Smirnov (KS) test, a permutation test, a Cramer-von Mises test, and any other statistical test (e.g., t-test, z-test, chi-squared test, test associated with distributions, etc.) can be used. In particular, one or more such statistical hypothesis tests can be used to assess a set of features having varying degrees of abundance in a first group of subjects exhibiting a target state (i.e., a sick state) and a second group of subjects not exhibiting the target state (i.e., having a normal state). In more detail, the set of features assessed can be constrained based upon percent abundance and/or any other suitable parameter pertaining to diversity in association with the first group of subjects and the second group of subjects, in order to increase or decrease confidence in the characterization. In a specific implementation of this example, a feature can be derived from a taxon of bacteria that is abundant in a certain percentage of subjects of the first group and subjects of the second group, where a relative abundance of the taxon between the first group of subjects and the second group of subjects can be determined from the KS test, with an indication of significance (e.g., in terms of p-value). Thus, an output of Block S130 can include a normalized relative abundance value (e.g., 25% greater abundance of a taxon in sick subjects vs. healthy subjects) with an indication of significance (e.g., a p-value of 0.0013). Variations of feature generation can additionally or alternatively implement or be derived from functional features or metadata features (e.g., non-bacterial markers). Additionally or alternatively, any suitable microbiome features can be derived based on statistical analyses (e.g., applied to a microorganism sequence dataset and/or other suitable microbiome dataset, etc.) including any one or more of: a prediction analysis, multi hypothesis testing, a random forest test, and principal component analysis.

In one example, migraine-related microbiome scores were determined using a random forest classifier for two or more sampling sites. In the particular example, the number of cases (individuals self-reporting experiencing migraines) and controls (individuals self-reporting not experience migraines) was included for each sampling site, as indicated on Table 1 for taxa abundance and Table 2 on for function prediction analyses. Optimal parameters found for XGBoost (according to Bayesian Parameter Optimization) are indicated in Table 3 for taxa abundance and Table 4 for function prediction analysis. Site-wise disease scores and prediction performances are indicated in Table 5 for taxa abundance and in Table 4 for function prediction analysis. In a specific example, for functional prediction analyses, a mean of 0.002 and a variance of 0.029 was determined, suggesting that the focal individual does not experience migraines as ascertained on the cases included in the study, which can be used to guide treatment and/or diagnoses:

TABLE 1

| Site | # Controls | # Cases |
|---|---|---|
| Gut | 2499 | 1319 |
| Nose | 2249 | 193 |
| Skin | 2058 | 164 |
| Mouth | 3559 | 277 |
| Genital | 1850 | 202 |

TABLE 2

| Site | # Controls | # Cases |
|---|---|---|
| Gut | 18365 | 1322 |
| Nose | 2298 | 109 |
| Skin | 2151 | 170 |
| Mouth | 3525 | 274 |
| Genital | 1845 | 200 |

TABLE 3

| Site | Max depth | Eta | N Rounds | Subsample % | By Tree % |
|---|---|---|---|---|---|
| Gut | 6 | 0.922 | 114.744 | 0.943 | 1.0 |
| Nose | 4 | 0.19 | 94.075 | 0.263 | 0.553 |
| Skin | 5 | 0.157 | 104.24 | 0.644 | 0.931 |
| Mouth | 4 | 0.107 | 109.699 | 0.990 | 0.742 |
| Genital | 6 | 0.1 | 70 | 1.0 | 1.0 |

TABLE 4

| Site | Max depth | Eta | N Rounds | Subsample % | By Tree % |
|---|---|---|---|---|---|
| Gut | 6 | 0.134 | 134.49 | 0.24 | 0.48 |
| Nose | 4 | 0.24 | 78.99 | 0.69 | 0.80 |
| Skin | 5 | 0.10 | 96.34 | 0.71 | 0.55 |
| Mouth | 4 | 0.12 | 130.63 | 0.22 | 0.79 |
| Genital | 6 | 0.34 | 115.91 | 0.66 | 0.48 |

TABLE 5

| Site | Mean | Standard Deviation | AUC |
|---|---|---|---|
| Gut | 0.024 | 0.05 | 0.79 |
| Nose | 0.103 | 0.126 | 0.574 |
| Skin | 0.020 | 0.010 | 0.46 |
| Mouth | 0.031 | 0.008 | 0.5 |
| Genital | 0.079 | 0.024 | 0.45 |

TABLE 6

| Site | Mean | Standard Deviation | AUC |
|---|---|---|---|
| Gut | 0.08 | 0.17 | 0.42 |
| Nose | 0.05 | 0.03 | 0.46 |
| Skin | 0.006 | 0.003 | 0.63 |
| Mouth | 0.010 | 0.008 | 0.55 |
| Genital | 0.001 | 0.001 | 0.49 |

In performing the characterization process, Block S130 can additionally or alternatively transform input data from at least one of the microbiome composition diversity dataset and microbiome functional diversity dataset into feature vectors that can be tested for efficacy in predicting characterizations of the population of subjects. Data from the supplementary dataset can be used to provide indication of one or more characterizations of a set of characterizations, where the characterization process is trained with a training dataset of candidate features and candidate classifications to identify features and/or feature combinations that have high degrees (or low degrees) of predictive power in accurately predicting a classification. As such, refinement of the characterization process with the training dataset identifies feature sets (e.g., of subject features, of combinations of features) having high correlation with specific classifications of subjects.

In variations, feature vectors (and/or any suitable set of features) effective in predicting classifications of the characterization process can include features related to one or more of: microbiome diversity metrics (e.g., in relation to distribution across taxonomic groups, in relation to distribution across archaeal, bacterial, viral, and/or eukaryotic groups), presence of taxonomic groups in one's microbiome, representation of specific genetic sequences (e.g., 16S sequences) in one's microbiome, relative abundance of taxonomic groups in one's microbiome, microbiome resilience metrics (e.g., in response to a perturbation determined from the supplementary dataset), abundance of genes that encode proteins or RNAs with given functions (enzymes, transporters, proteins from the immune system, hormones, interference RNAs, etc.) and any other suitable features derived from the microbiome diversity dataset and/or the supplementary dataset. In variations, microbiome features can be associated with (e.g., include, correspond to, typify, etc.) at least one of: presence of a microbiome feature from the microbiome features, absence of the microbiome features from the microbiome features, relative abundance of different taxonomic groups associated with the headache-related condition; a ratio between at least two microbiome features associated with the different taxonomic groups, interactions between the different taxonomic groups, and phylogenetic distance between the different taxonomic groups. In a specific example, microbiome features can include one or more relative abundance characteristics associated with at least one of the microbiome composition diversity features (e.g., relative abundance associated with different taxa, etc.) and the microbiome functional diversity features (e.g., relative abundance of sequences corresponding to different functional features; etc.). Relative abundance characteristics and/or other suitable microbiome features (and/or other suitable data described herein) can be extracted and/or otherwise determined based on: a normalization, a feature vector derived from at least one of linear latent variable analysis and non-linear latent variable analysis, linear regression, non-linear regression, a kernel method, a feature embedding method, a machine learning method, and a statistical inference method. Additionally or alternatively, combinations of features can be used in a feature vector, where features can be grouped and/or weighted in providing a combined feature as part of a feature set. For example, one feature or feature set can include a weighted composite of the number of represented classes of bacteria in one's microbiome, presence of a specific genus of bacteria in one's microbiome, representation of a specific 16S sequence in one's microbiome, and relative abundance of a first phylum over a second phylum of bacteria. However, the feature vectors can additionally or alternatively be determined in any other suitable manner.

Figure 3:
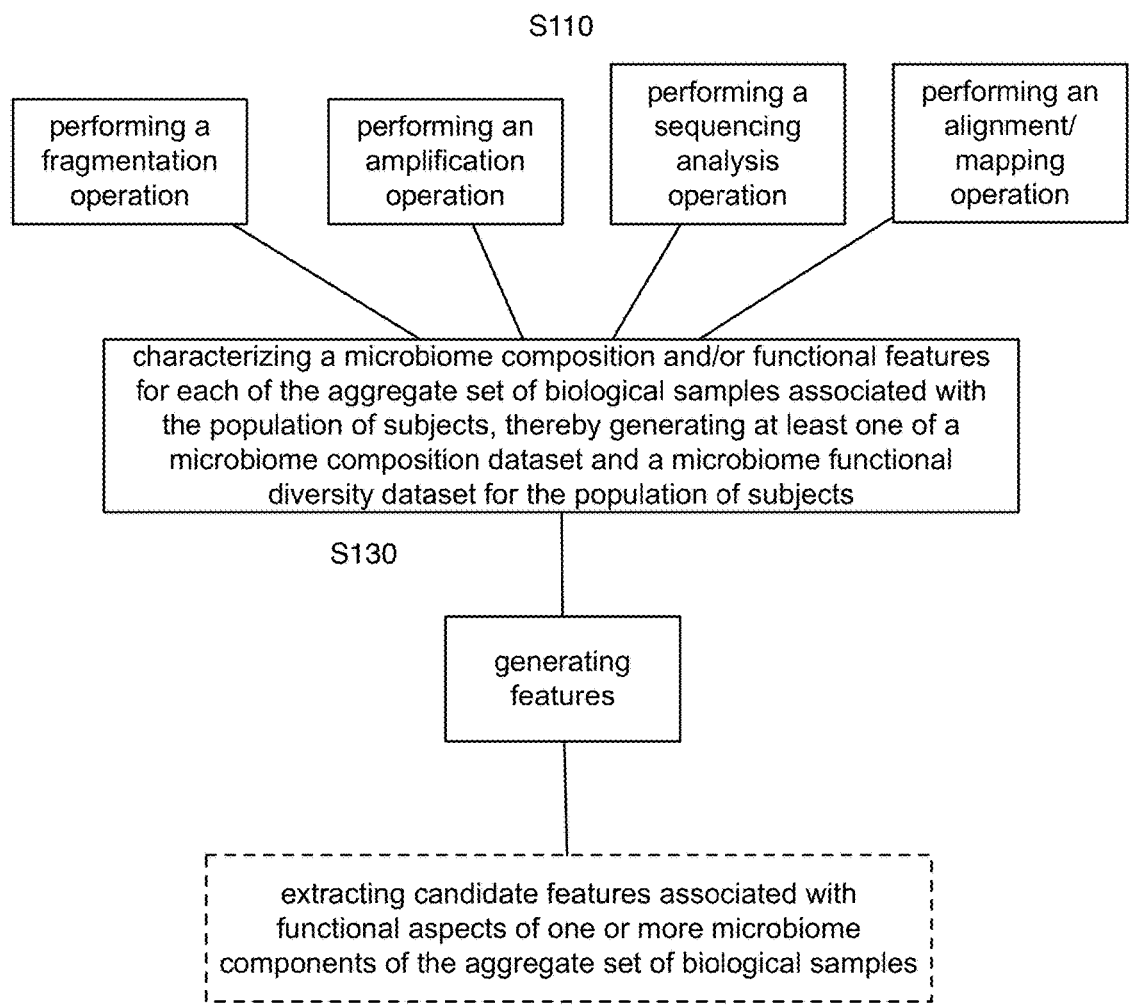
FIG. 3 depicts a variation of a process for generation of a characterization model in an embodiment of a method.

As shown in FIG. 3, in one such alternative variation of Block S130, the characterization process can be generated and trained according to a random forest predictor (RFP) algorithm that combines bagging (i.e., bootstrap aggregation) and selection of random sets of features from a training dataset to construct a set of decision trees, T, associated with the random sets of features. In using a random forest algorithm, N cases from the set of decision trees are sampled at random with replacement to create a subset of decision trees, and for each node, m prediction features are selected from all of the prediction features for assessment. The prediction feature that provides the best split at the node (e.g., according to an objective function) is used to perform the split (e.g., as a bifurcation at the node, as a trifurcation at the node). By sampling many times from a large dataset, the strength of the characterization process, in identifying features that are strong in predicting classifications can be increased substantially. In this variation, measures to prevent bias (e.g., sampling bias) and/or account for an amount of bias can be included during processing to increase robustness of the model.

Additionally or alternatively, Block S130 (e.g., extracting microbiome features; generating characterization models for headache-related conditions; etc.) and/or other suitable portions of the method 100 (e.g., determining a headache-related characterization; determining and/or providing a therapy; etc.) can employ data processing approaches including any one or more of: performing pattern recognition on data (e.g., identifying correlations between headache-related conditions and microbiome features; etc.), fusing data from multiple sources (e.g., generating characterization models based on microbiome data and/or supplementary data from a plurality of users associated with one or more headache-related conditions; etc.), combination of values (e.g., averaging values, etc.), compression, conversion (e.g., digital-to-analog conversion, analog-to-digital conversion), performing statistical estimation on data (e.g. ordinary least squares regression, non-negative least squares regression, principal components analysis, ridge regression, etc.), wave modulation, normalization, updating (e.g., of characterization models and/or therapy models based on processed biological samples over time; etc.), ranking (e.g., microbiome features; therapies; etc.), weighting (e.g., microbiome features; etc.), validating, filtering (e.g., for baseline correction, data cropping, etc.), noise reduction, smoothing, filling (e.g., gap filling), aligning, model fitting, binning, windowing, clipping, transformations, mathematical operations (e.g., derivatives, moving averages, summing, subtracting, multiplying, dividing, etc.), data association, multiplexing, demultiplexing, interpolating, extrapolating, clustering, image processing techniques, other signal processing operations, other image processing operations, visualizing, and/or any other suitable processing operations. However, data processing for facilitating any suitable portions of the method 100 can be performed in any suitable manner.

In a variation, Block S130 and/or other portions of the method 100 can include applying computer-implemented rules (e.g., models, feature selection rules, etc.) to process population-level data, but can additionally or alternatively include applying computer-implemented rules to process microbiome-related data on a demographic-specific basis (e.g., subgroups sharing a demographic feature such as headache-relation conditions therapy regiments, dietary regiments, physical activity regiments, ethnicity, age, gender, weight, sleeping behaviors, etc.), condition-specific basis (e.g., subgroups exhibiting a specific migraine condition, a specific headache-related condition, a combination of headache-related conditions, triggers for the headache-related conditions, associated symptoms, etc.), a sample type-specific basis (e.g., applying different computer-implemented rules to process microbiome data derived from different collection sites; etc.), a user basis (e.g., different computer-implemented rules for different users; etc.) and/or any other suitable basis. As such, Block S132 can include assigning users from the population of users to one or more subgroups; and applying different computer-implemented rules for determining features (e.g., the set of feature types used; the types of characterization models generated from the features; etc.) for the different subgroups. However, applying computer-implemented rules can be performed in any suitable manner.

In another variation, Block S130 can include processing (e.g., generating, training, updating, executing, storing, etc.) one or more characterization models (e.g., headache-related condition characterization models, etc.) for one or more headache-related conditions. The characterization models preferably leverage microbiome features as inputs, and preferably output headache-related characterizations and/or any suitable components thereof; but characterization models can use and suitable inputs to generate any suitable outputs. In an example, Block S130 can include transforming the supplementary data, the microbiome composition diversity features, and the microbiome functional diversity features into a characterization model (e.g., training the characterization model based on the supplementary data and microbiome features; etc.) for the headache-related condition. In another example, the method 100 can include: determining a population microorganism sequence dataset (e.g., including microorganism sequence outputs for different users of the population; etc.) for a population of users associated with one or more headache-related conditions, based on a set of samples from the population of users (e.g., and/or based on one or more primer types associated with the headache-related condition; etc.); collecting a supplementary dataset associated with diagnosis of the one or more headache-related conditions for the population of subjects; and generating the headache-related condition characterization model based on the population microorganism sequence dataset and the supplementary dataset.

Figure 8:
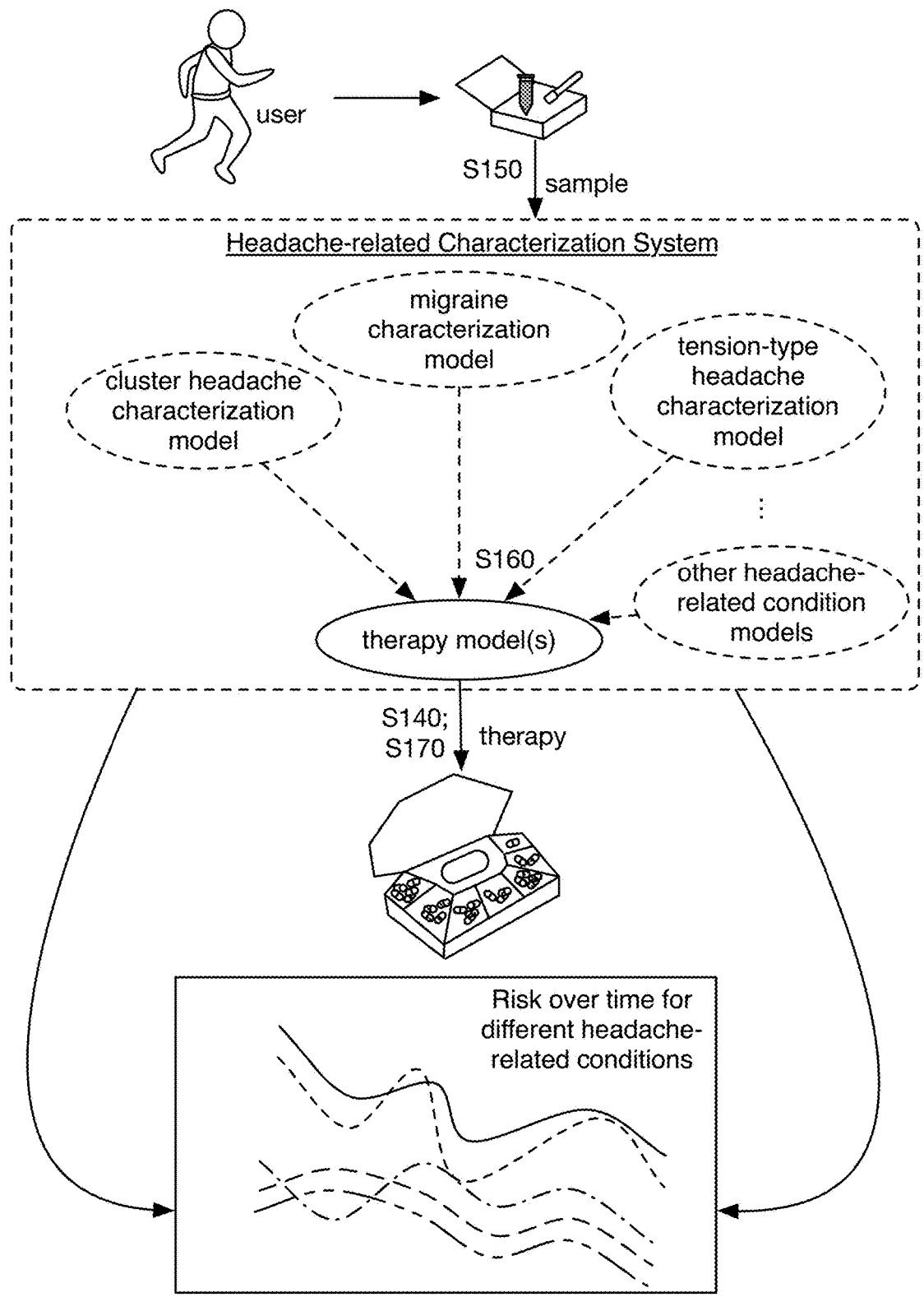
FIG. 8 depicts variations of promoting a therapy in an embodiment of a method.

In another variation, as shown in FIG. 8, different characterization models and/or other suitable models (e.g., generated with different algorithms, with different sets of features, with different input and/or output types, applied in different manners such as in relation to time, frequency, component applying the model, etc.) can be generated for different demographic groups (e.g., a first characterization model for users on a dietary regimen including food items associated with the headache-related condition, and a second characterization model for users on a dietary regimen not including the food items; different models based on physical activity level; different models based on age, gender, weight, height, ethnicity; etc.), headache-related conditions (e.g., different characterization models for users with different headache-related conditions; etc.), individual users, supplementary data (e.g., models incorporating features derived from biometric sensor data and/or survey response data vs. models independent of supplementary data, etc.), and/or other suitable criteria. However, performing a characterization process S130 can be performed in any suitable manner.

3.3.A Headache-related Characterization Process.

A characterization process of Block S130 based upon statistical analyses can identify the sets of features that have the highest correlations with a migraine condition and/or other suitable headache-related conditions for which one or more therapies would have a positive effect, such as based upon a random forest predictor algorithm trained with a training dataset derived from a subset of the population of subjects, and validated with a validation dataset derived from a subset of the population of subjects; and/or through any other suitable approaches described herein. In particular, a migraine condition can include a complex disorder characterized by recurrent headaches that are moderate to severe, characterized by five or more attacks, four hours to three days in duration, two or more of the following: unilateral pain, pulsating pain, moderate or severe pain intensity, worsened by or causing avoidance of routine physical activity; plus one or more of the following: Nausea and/or vomiting, sensitivity to light (photophobia) and sound (phonophobia). Microbiome features (e.g., microbiome composition diversity features; etc.) associated with one or more migraine conditions and/or other suitable headache-related conditions (e.g., features useful for diagnostics) can include microbiome features associated with one or more of the following taxons: Ruminococcaceae (family), *Clostridium* (genera) (e.g., *Clostridium*_1485), *Parabacteroides* (genera) (e.g., *Parabacteroides*_375288), and/or any other suitable taxonomic groups. Microbiome features (e.g., microbiome functional diversity features) associated with one or more migraine conditions and/or other suitable headache-related conditions can additionally or alternatively include microbiome features associated with at least one of: Carbohydrate Metabolism, Metabolism, Lipid Metabolism, Translation, Xenobiotics Biodegradation and Metabolism, Environmental Adaptation, Cell Motility, Enzyme Families, Metabolism of Cofactors and Vitamins, Nucleotide Metabolism, Replication and Repair, Pyruvate metabolism, Amino acid metabolism, Chloroalkane and chloroalkene degradation, Ribosome biogenesis in eukaryotes, Pentose and glucuronate interconversions, Terpenoid backbone biosynthesis, Biosynthesis and biodegradation of secondary metabolites, Riboflavin metabolism, Ribosome Biogenesis, Other transporters, Glyoxylate and dicarboxylate metabolism, Carbohydrate metabolism, Others, Fructose and mannose metabolism, Chromosome, Galactose metabolism, One carbon pool by folate, Amino acid related enzymes, Pyrimidine metabolism, Ribosome, Aminoacyl-tRNA biosynthesis, Tuberculosis, Homologous recombination, Fatty acid biosynthesis, Cysteine and methionine metabolism, Plant-pathogen interaction, Pentose phosphate pathway, Peptidoglycan biosynthesis, Prenyltransferases, Translation factors, Translation proteins, Nicotinate and nicotinamide metabolism, Photosynthesis proteins, Photosynthesis, Phosphatidylinositol signaling system, DNA repair and recombination proteins, Nucleotide excision repair, Bacterial toxins, Bacterial chemotaxis, RNA polymerase, Naphthalene degradation, Peptidases and/or any other suitable functional aspects. Functional features can include and/or otherwise be associated with any one or more of: a Kyoto Encyclopedia of Genes and Genomes (KEGG) functional feature and a Clusters of Orthologous Groups (COG) functional feature. Thus, characterization of the subject includes characterization of the subject as someone with a migraine condition and/or other suitable headache-related conditions based upon detection of one or more of the above features, in a manner that is an alternative or supplemental to typical methods of diagnosis. In variations of the specific example, the set of features can, however, include any other suitable features useful for diagnostics.

In variations, determining headache-related characterizations and/or any other suitable characterizations for conditions associated with microorganisms can include determining headache-related characterizations in relation to specific physiological sites (e.g., gut, healthy gut, skin, nose, mouth, genitals, other suitable physiological sites, other sample collection sites, etc.), such as through any one or more of: determining a headache-related characterization based on a headache-related characterization model derived based on site-specific data (e.g., defining correlations between a headache-related condition and microbiome features associated with one or more physiological sites); determining a headache-related characterization based on a user biological sample collected at one or more physiological sites, and/or any other suitable site-related processes. In examples, machine learning approaches (e.g., classifiers, deep learning algorithms), statistical tests, dimension reduction approaches, and/or other suitable approaches (e.g., described herein) can be applied in determining site-related (e.g., physiological site-related, etc.) characterizations, other suitable characterizations, therapies, and/or any other suitable outputs. However, the method 100 can include determining any suitable site-related (e.g., site-specific) outputs, and/or performing any suitable portions of the method 100 (e.g., collecting samples, processing samples, determining therapies) with site-specificity and/or other site-relatedness in any suitable manner.

Characterization of the subject(s) can additionally or alternatively implement use of a high false positive test and/or a high false negative test to further analyze sensitivity of the characterization process in supporting analyses generated according to embodiments of the method 100.

However, applying a characterization process in relation to headache-related conditions can be performed in any suitable manner.

3.4 Method—Determining a Therapy Model.

The method 100 can additionally or alternatively include Block S140, which recites: determining a therapy model for determining therapies for preventing, ameliorating, and/or otherwise modifying one or more headache-related conditions. Block S140 can function to identify or predict one or more therapies (e.g., probiotic-based therapies, phage-based therapies, small molecule-based therapies, etc.) that can shift a subject's microbiome composition and/or functional features toward a desired equilibrium state in promotion of the subject's health. For example, therapies (e.g., determined in Block S140, promoted in Block S170, etc.) can enable (e.g., facilitate, cause, etc.) selective modulation of a microbiome of the user in relation to at least one of: a population size of a desired taxon, a population size of a desired microbiome function, another microbiome composition aspect (e.g., related to a microbiome composition feature), a microbiome functional aspect (e.g., related to a microbiome functional feature; etc.) in association with improving a state of the headache-related condition. In Block S140, the therapies can be selected from therapies including one or more of: probiotic therapies, phage-based therapies, small molecule-based therapies, cognitive/behavioral therapies, physical rehabilitation therapies, clinical therapies, medication-based therapies, diet-related therapies, and/or any other suitable therapy designed to operate in any other suitable manner in promoting a user's health. In examples, medication-based therapies can include recommendations for at least one of a: medication type, a medication dosage, medication schedule (e.g., for consuming medications), and/or other suitable medication-related aspects, in association with one or more headache-related medications operable to improve a state of the headache-related condition. Headache-related medications can include any one o more of: antipsychotics; pain relievers (e.g., Chlorpromazine Analgesic); Naproxen; Sumatriptan (Treximet); Caffeine; Ergotamine; Acetaminophen (e.g., Tylenol, Mapap, Feverall, Acephen, and Nortemp); Non-steroidal anti-Inflammatory drugs; stimulants; nerve pain medication; Neurotoxin; and/or any other suitable medication-based therapy.

In a specific example of a bacteriophage-based therapy, one or more populations (e.g., in terms of colony forming units) of bacteriophages specific to a certain bacteria (or other microorganism) represented in the subject can be used to down-regulate or otherwise eliminate populations of the certain bacteria. As such, bacteriophage-based therapies can be used to reduce the size(s) of the undesired population(s) of bacteria represented in the subject. Complementarily, bacteriophage-based therapies can be used to increase the relative abundances of bacterial populations not targeted by the bacteriophage(s) used.

Figure 4:
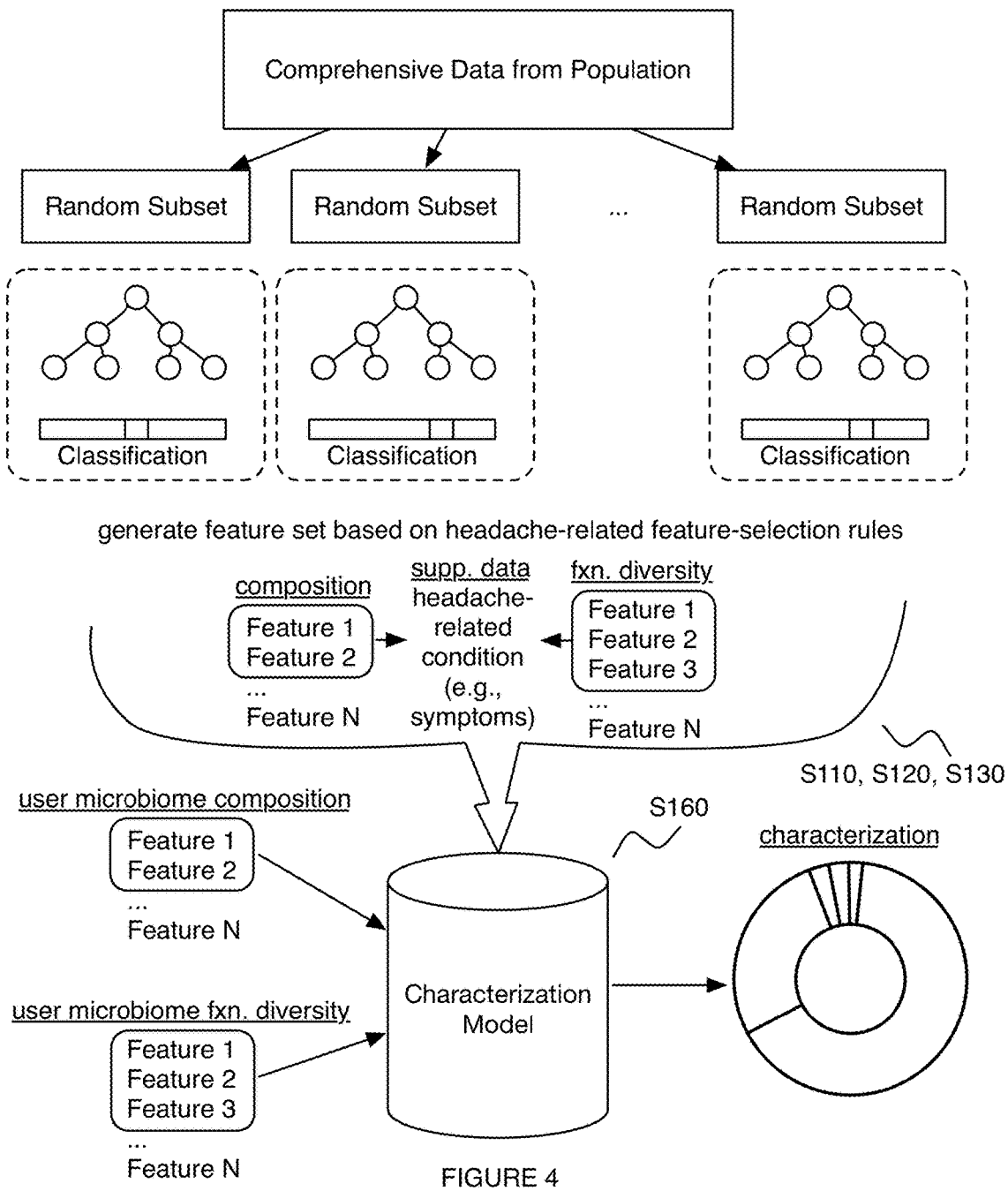
FIG. 4 depicts variations of mechanisms by which probiotic-based therapies operate in an embodiment of a method.

In another specific example of probiotic therapies, as shown in FIG. 4, candidate therapies of the therapy model can perform one or more of: blocking pathogen entry into an epithelial cell by providing a physical barrier (e.g., by way of colonization resistance), inducing formation of a mucous barrier by stimulation of goblet cells, enhance integrity of apical tight junctions between epithelial cells of a subject (e.g., by stimulating up regulation of zona-occludens 1, by preventing tight junction protein redistribution), producing antimicrobial factors, stimulating production of anti-inflammatory cytokines (e.g., by signaling of dendritic cells and induction of regulatory T-cells), triggering an immune response, and performing any other suitable function that adjusts a subject's microbiome away from a state of dysbiosis.

In another specific example, therapies can include medical-device based therapies (e.g., nerve stimulation-based devices; electrode-based devices; headwear devices; etc.).

In variations, the therapy model is preferably based upon data from a large population of subjects, which can include the population of subjects from which the microbiome diversity datasets are derived in Block S110, where microbiome composition and/or functional features or states of health, prior exposure to and post exposure to a variety of therapeutic measures, are well characterized. Such data can be used to train and validate the therapy provision model, in identifying therapeutic measures that provide desired outcomes for subjects based upon different microbiome characterizations. In variations, support vector machines, as a supervised machine learning algorithm, can be used to generate the therapy provision model. However, any other suitable machine learning algorithm described above can facilitate generation of the therapy provision model.

While some methods of statistical analyses and machine learning are described in relation to performance of the Blocks above, variations of the method 100 (e.g., any suitable Blocks of the method 100; characterization models; therapy models; etc.) can additionally or alternatively utilize any other suitable algorithms in performing the characterization process. In variations, the algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the algorithm(s) can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of algorithm.

Additionally or alternatively, the therapy model (and/or other suitable models) can be derived in relation to identification of a "normal" or baseline microbiome composition and/or functional features, as assessed from subjects of a population of subjects who are identified to be in good health. Upon identification of a subset of subjects of the population of subjects who are characterized to be in good health (e.g., using features of the characterization process), therapies that modulate microbiome compositions and/or functional features toward those of subjects in good health can be generated in Block S140. Block S140 can thus include identification of one or more baseline microbiome compositions and/or functional features (e.g., one baseline microbiome for each of a set of demographics), and potential therapy formulations and therapy regimens that can shift microbiomes of subjects who are in a state of dysbiosis toward one of the identified baseline microbiome compositions and/or functional features. The therapy model can, however, be generated and/or refined in any other suitable manner.

Microorganism compositions associated with probiotic therapies associated with the therapy model preferably include microorganisms that are culturable (e.g., able to be expanded to provide a scalable therapy) and non-lethal (e.g., non-lethal in their desired therapeutic dosages). Furthermore, microorganism compositions can include a single type of microorganism that has an acute or moderated effect upon a subject's microbiome. Additionally or alternatively, microorganism compositions can include balanced combinations of multiple types of microorganisms that are configured to cooperate with each other in driving a subject's microbiome toward a desired state. For instance, a combination of multiple types of bacteria in a probiotic therapy can include a first bacteria type that generates products that are used by a second bacteria type that has a strong effect in positively affecting a subject's microbiome. Additionally or alternatively, a combination of multiple types of bacteria in a probiotic therapy can include several bacteria types that produce proteins with the same functions that positively affect a subject's microbiome.

Probiotic compositions can be naturally or synthetically derived. For instance, in one application, a probiotic composition can be naturally derived from fecal matter or other biological matter (e.g., of one or more subjects having a baseline microbiome composition and/or functional features, as identified using the characterization process and the therapy model). Additionally or alternatively, probiotic compositions can be synthetically derived (e.g., derived using a benchtop method) based upon a baseline microbiome composition and/or functional features, as identified using the characterization process and the therapy model. In variations, microorganism agents that can be used in probiotic therapies can include one or more of: yeast (e.g., *Saccharomyces boulardii*), gram-negative bacteria (e.g., *E. coli* Nissle), gram-positive bacteria (e.g., *Bifidobacteria bifidum, Bifidobacteria infantis, Lactobacillus rhamnosus, Lactococcus lactis, Lactobacillus plantarum, Lactobacillus acidophilus, Lactobacillus casei, Bacillus polyfermenticus*, etc.), and any other suitable type of microorganism agent. In specific examples, probiotic therapies can include probiotic compositions operable to modulate taxonomic groups associated with headache-related microbiome composition features (e.g., described herein), such as through including microorganisms of the taxonomic groups, microorganisms operable to modify populations of other microorganisms of the taxonomic groups, and/or through any suitable manner.

In a variation, for subjects who exhibit migraine, a probiotic therapy can include a combination of one or more of: *Parabacteroides* genera provided at dosages of 1 million to 10 billion CFUs, as determined from a therapy model that predicts positive adjustment of a patient's microbiome in response to the therapy. In the first specific example, a subject can be instructed to ingest capsules including the probiotic formulation according to a regimen tailored to one or more of his/her: physiology (e.g., body mass index, weight, height), demographics (e.g., gender, age), severity of dysbiosis, sensitivity to medications, and any other suitable factor. Additionally or alternatively, any suitable approaches and/or components described in relation to therapy models can be analogously applied to any other suitable models (e.g., characterization models), and/or approaches and/or components described in relation to other models can be analogously applied to therapy models. However, Block S140 can be performed in any suitable manner.

3.5 Method—Processing a User Biological Sample.

The method 100 can additionally or alternatively include Block S150, which recites: processing one or more biological samples from a user (e.g., subject). Block S150 can function to facilitate generation of a microbiome dataset for the subject that can be used to derive inputs for the characterization process (e.g., for generating a headache-related characterization for the user, etc.). As such, Block S150 can include receiving, processing, and/or analyzing one or more biological samples from one or more users (e.g., multiple biological samples for the same user over time, different biological samples for different users, etc.). In Block S150, the biological sample is preferably generated from the subject and/or an environment of the subject in a non-invasive manner. In variations, non-invasive manners of sample reception can use any one or more of: a permeable substrate (e.g., a swab configured to wipe a region of a subject's body, toilet paper, a sponge, etc.), a non-permeable substrate (e.g., a slide, tape, etc.) a container (e.g., vial, tube, bag, etc.) configured to receive a sample from a region of a subject's body, and any other suitable sample-reception element. In a specific example, the biological sample can be collected from one or more of the subject's nose, skin, genitals, mouth, and gut in a non-invasive manner (e.g., using a swab and a vial). However, the biological sample can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can include blood samples, plasma/serum samples (e.g., to enable extraction of cell-free DNA), and tissue samples.

In the above variations and examples, the biological sample can be taken from the body of the subject without facilitation by another entity (e.g., a caretaker associated with a subject, a health care professional, an automated or semi-automated sample collection apparatus, etc.), or can alternatively be taken from the body of the subject with the assistance of another entity. In one example, where the biological sample is taken from the subject without facilitation by another entity in the sample extraction process, a sample-provision kit can be provided to the subject. In the example, the kit can include one or more swabs for sample acquisition, one or more containers configured to receive the swab(s) for storage, instructions for sample provision and setup of a user account, elements configured to associate the sample(s) with the subject (e.g., barcode identifiers, tags, etc.), and a receptacle that allows the sample(s) from the subject to be delivered to a sample processing operation (e.g., by a mail delivery system). In another example, where the biological sample is extracted from the subject with the help of another entity, one or more samples can be collected in a clinical or research setting from the subject (e.g., during a clinical appointment). The biological sample can, however, be received from the subject in any other suitable manner.

Furthermore, processing and analyzing the biological sample (e.g., to generate a user microbiome dataset; etc.) from the subject is preferably performed in a manner similar to that of one of the embodiments, variations, and/or examples of sample reception described in relation to Block S110 above, and/or any other suitable portions of the method 100. As such, reception and processing of the biological sample in Block S150 can be performed for the subject using similar processes as those for receiving and processing biological samples used to generate the characterization process and/or the therapy model of the method 100, in order to provide consistency of process. However, biological sample reception and processing in Block S150 can alternatively be performed in any other suitable manner.

3.6 Determining a Headache-related Characterization.

The method 100 can additionally or alternatively include Block S160, which recites: determining, with the characterization process, a headache-related characterization for the user based upon processing a microbiome dataset (e.g., user microorganism sequence dataset, microbiome composition dataset, microbiome functional diversity dataset, etc.) derived from the biological sample of the user. Block S160 can function to characterize one or more headache-related conditions for a user, such as through extracting features from microbiome-derived data of the subject, and using the features as inputs into an embodiment, variation, or example of the characterization process described in Block S130 above. In an example, Block S160 can include generating a headache-related characterization for the user based on user microbiome features and a headache-related condition characterization model (e.g., generated in Block S130). Headache-related characterizations can be for any number and/or combination of headache-related conditions (e.g., multiple migraine conditions, a combination of headache-related conditions, a single headache-related conditions, diseases and/or other conditions associated with migraine and/or other suitable headache-related conditions; etc.). Headache-related characterizations can include one or more of: diagnoses (e.g., presence or absence of a headache-related condition; etc.); risk (e.g., risk scores for developing and/or the presence of a headache-related condition; information regarding headache-related characterizations (e.g., symptoms, signs, triggers, associated conditions, etc.); comparisons (e.g., comparisons with other subgroups, populations, users, historic health statuses of the user such as historic microbiome compositions and/or functional diversities; comparisons associated with headache-related conditions; etc.), and/or any other suitable headache-related data.

Figure 7:
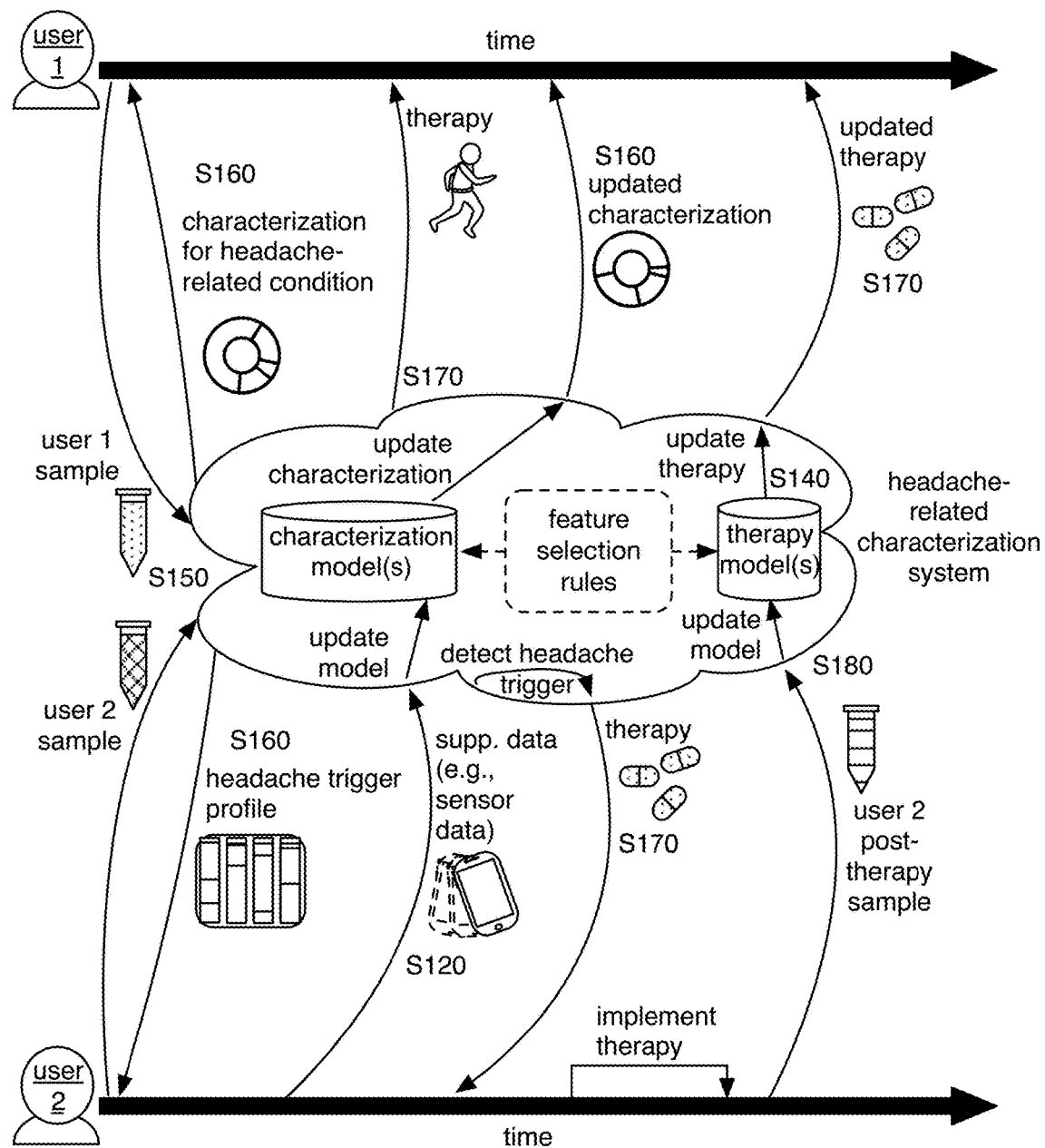
FIG. 7 depicts a schematic representation of variations of an embodiment of the method.

In a variation, as shown in FIG. 7, headache-related characterization can include one or more headache-related (e.g., migraine) trigger profiles for the user, where the trigger profile can describe headache triggers (e.g., conditions correlated with headache-related symptoms; conditions indicating future headache-related conditions; causes; etc.) associated with the user (e.g., known to affect the user; predicted to affect the user, such as based on microbiome features, supplementary data, etc.). Headache triggers can include any one or more of: dietary triggers (e.g., caffeine, alcohol, food additives, salty foods, dietary habits, missing meals, too many meals, etc.); hormonal changes; stress; sensory stimuli (e.g., lights, sounds, smells, etc.); sleep triggers (e.g., sleep deprivation, sleep abundance, etc.); physical activity (e.g., excess physical activity, etc.); environmental triggers (e.g., weather, barometric pressure, etc.); medication-based triggers (e.g., contraceptives, vasodilators, etc.); and/or any other suitable triggers. Headache triggers and/or other headache-related conditions can be associated with (e.g., correlated with, etc.) one or more of: family history, age, gender, weight, height, other demographic characteristics, and/or any other suitable supplementary data. In a specific example, generating a headache-related characterization can include generating a migraine trigger profile for the user based on user microbiome features (e.g., and a headache-related condition characterization model), and promoting (e.g., providing) a therapy operable to reduce migraine triggers indicated by the migraine trigger profile for the user. In examples, the method 100 can include detecting headache triggers (e.g., migraine triggers) for a user based on a corresponding headache-related trigger profile (e.g., for the user, for another user, etc.). In a specific example, the method 100 can include: detecting a migraine trigger based on the migraine trigger profile and user supplementary data including at least one of motion sensor data and location sensor data (e.g., indicating physical activity behaviors; user locations; mobility behaviors; other behaviors correlated with headache triggers; etc.) collected from a mobile computing device (e.g., smartphone, smart watch, tablet, laptop, etc.) associated with the user; and promoting a therapy in response to detecting the migraine trigger (and/or other suitable headache triggers; etc.). Additionally or alternatively, detecting headache triggers in relation to a headache-related trigger profile can be based on any one or more of: microbiome features (e.g., a microbiome composition indicating a high risk of a migraine in response to certain headache triggers; a microbiome functional diversity indicating a high risk of a headache-related symptom during a future time period, such as within the next 24 hours, etc.), supplementary features (e.g., historic medical data for the user, sensor data, nutrition supplementary data, sleep data such as derived through sensor data, etc.), and/or any other suitable features.

In another variation, a headache-related characterization can include a microbiome diversity score (e.g., in relation to microbiome composition, function, etc.) associated with (e.g., correlated with; negatively correlated with; positively correlated with; etc.) a microbiome diversity score correlated with the headache-related condition. In an example, the method 100 can include promoting a nutrition-related therapy (e.g., probiotics; dietary regimen modifications; etc.) operable to improve the microbiome diversity score for improving a state of the headache-related condition, such as based on a headache-related characterization (e.g., including the microbiome diversity score for the user) and/or nutrition-related supplementary data collected from the user. In examples, the headache-related characterization can include microbiome diversity scores over time (e.g., calculated for a plurality of biological samples of the user collected over time), comparisons to microbiome diversity scores for other users, and/or any other suitable type of microbiome diversity score. However, processing microbiome diversity scores (e.g., determining microbiome diversity scores; using microbiome diversity scores to determine and/or provide therapies; etc.) can be performed in any suitable manner.

Determining a headache-related characterization in Block S160 preferably includes identifying features and/or combinations of features associated with the microbiome composition and/or functional features of the subject, inputting the features into the characterization process, and receiving an output that characterizes the subject as belonging to one or more of: a behavioral group, a gender group, a dietary group, a disease-state group, and any other suitable group capable of being identified by the characterization process. Block S160 can additionally or alternatively include generation of and/or output of a confidence metric associated with the characterization of the subject. For instance, a confidence metric can be derived from the number of features used to generate the characterization, relative weights or rankings of features used to generate the characterization, measures of bias in the characterization process, and/or any other suitable parameter associated with aspects of the characterization process. However, leveraging user microbiome features can be performed in any suitable manner to generate any suitable headache-related characterizations.

In some variations, features extracted from the microbiome dataset of the subject can be supplemented with supplementary features (e.g., extracted from supplementary data collected for the user; such as survey-derived features, medical history-derived features, sensor data, etc.), where such data, the user microbiome data, and/or other suitable data can be used to further refine the characterization process of Block S130, Block S160, and/or other suitable portions of the method 100.

Determining a headache-related characterization preferably includes extracting and applying user microbiome features (e.g., user microbiome composition diversity features; user microbiome functional diversity features; etc.) for the user (e.g., based on a user microbiome dataset), characterization models, and/or other suitable components, such as by employing approaches described in Block S130, and/or by employing any suitable approaches described herein.

Figure 6:
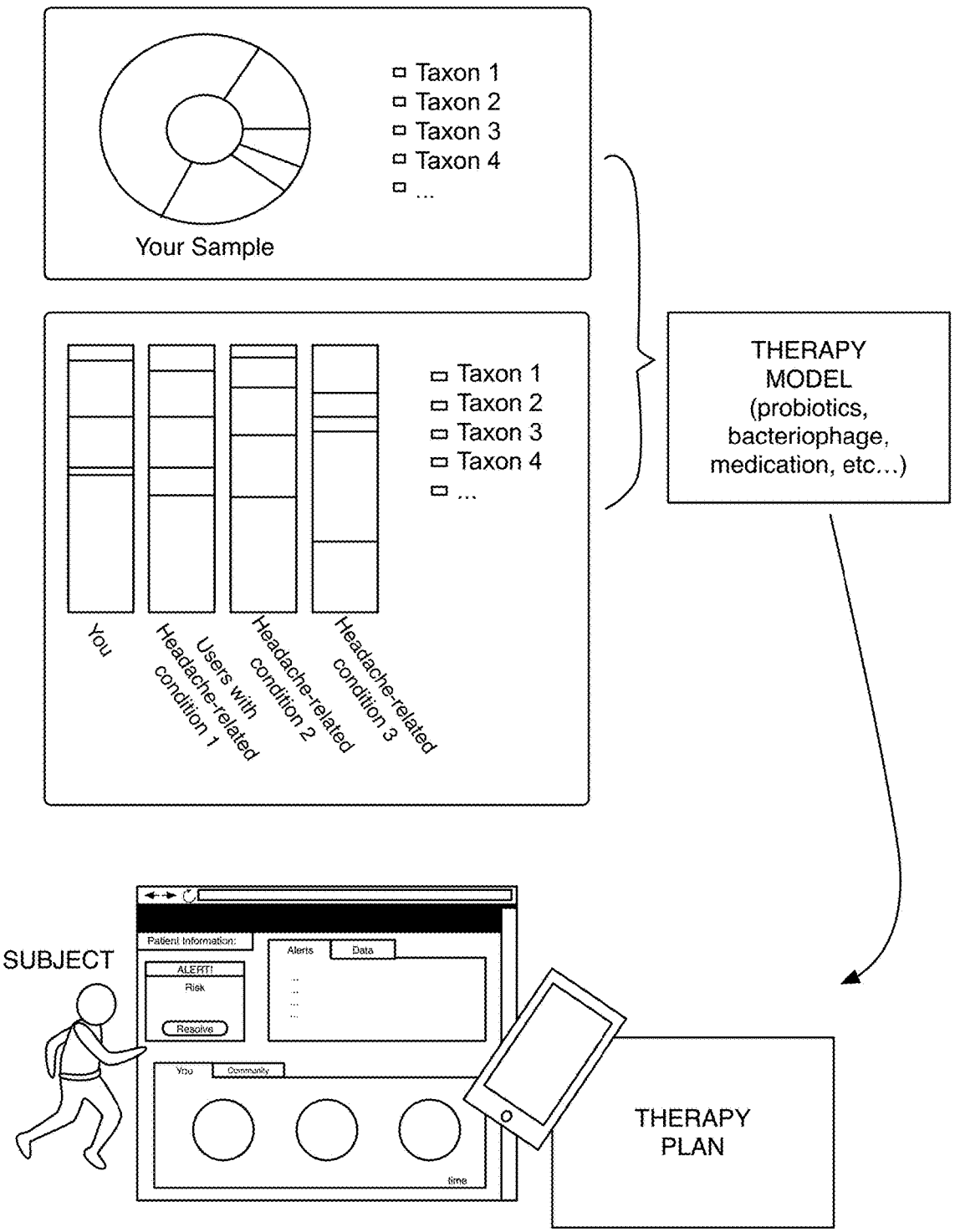
FIG. 6 depicts a schematic representation of variations of an embodiment of the method.

In variations, as shown in FIG. 6, Block S160 can include presenting headache-related characterizations (e.g., information extracted from the characterizations, etc.), such as an a web interface, a mobile application, and/or any other suitable interface, but presentation of headache-related information can be performed in any suitable manner. However, the microbiome dataset of the subject can additionally or alternatively be used in any other suitable manner to enhance the models of the method 100, and Block S160 can be performed in any suitable manner.

3.7 Method—Promoting a Therapy.

Figure 5:
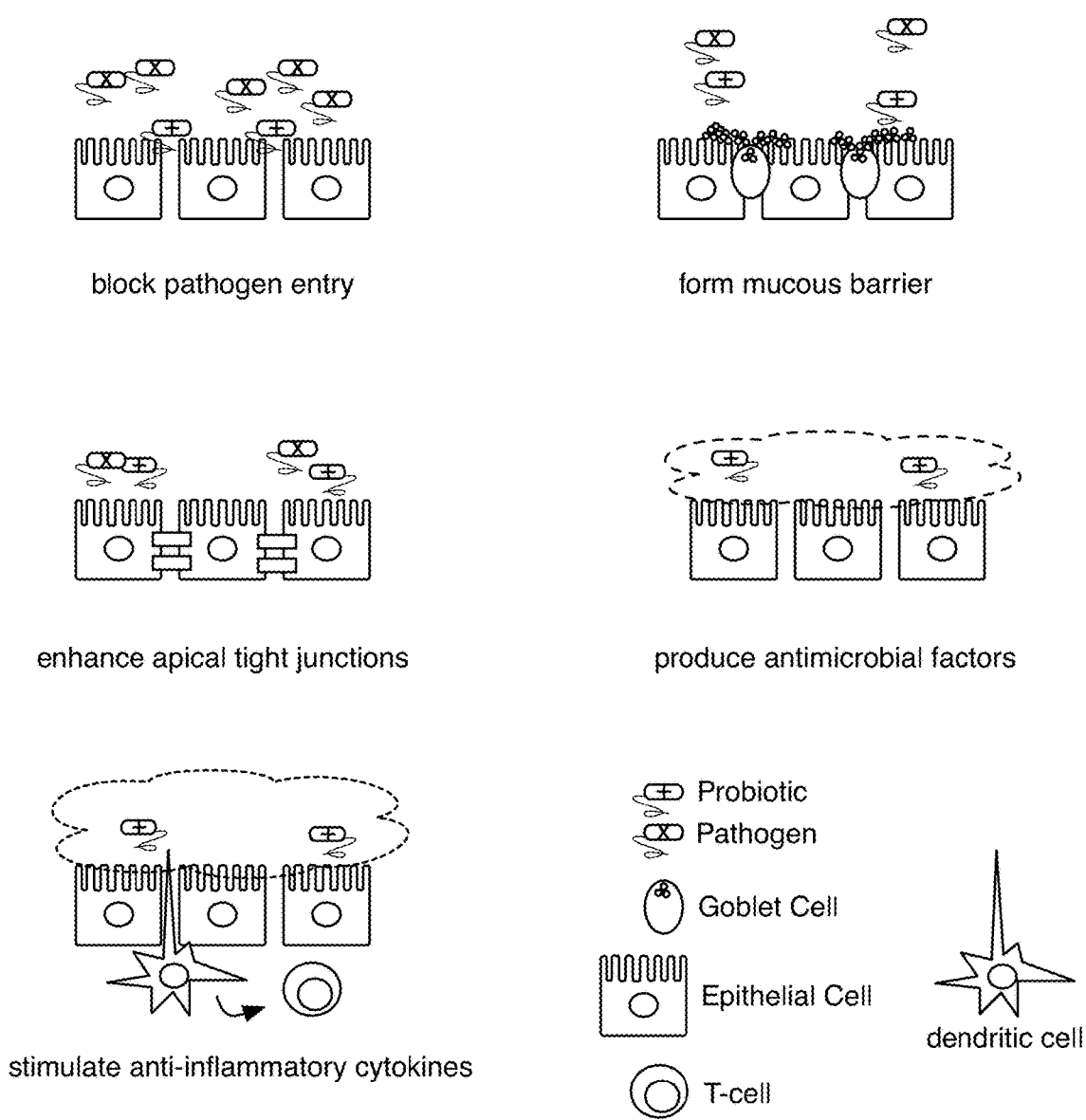
FIG. 5 depicts examples of notification provision in a specific example.
Figure 9:
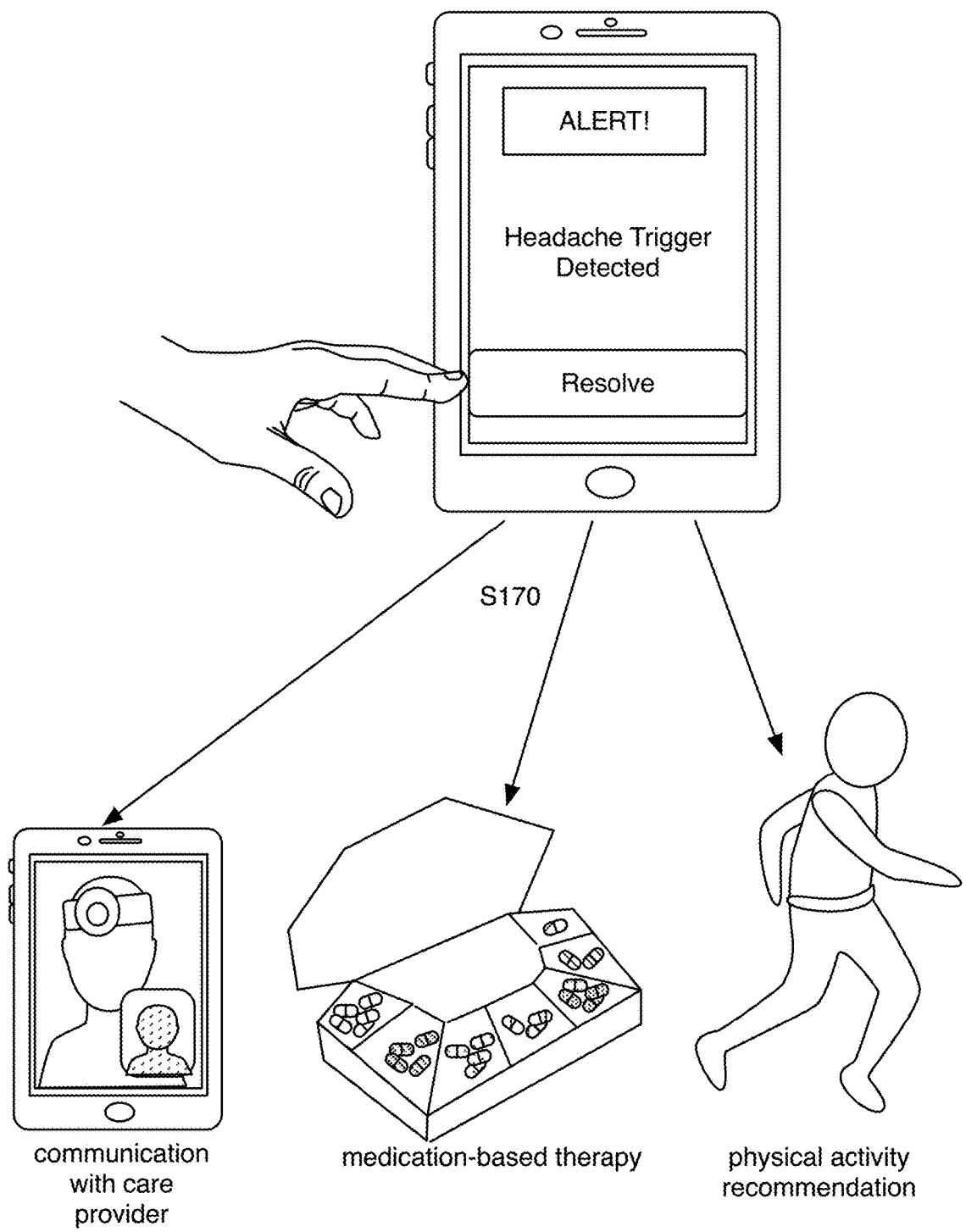
FIG. 9 depicts an example of promoting a therapy in an embodiment of a method.

As shown in FIG. 9, the method 100 can additionally or alternatively include Block S110, which recites: promoting (e.g., providing, facilitating provision of, etc.) a therapy for the headache-related condition to the user (e.g., based upon the headache-related characterization and/or a therapy model). Block S110 can function to recommend or provide a personalized therapy to the subject, in order to shift the microbiome composition and/or functional diversity of a user toward a desired equilibrium state. Block S110 can include provision of a customized therapy to the subject according to their microbiome composition and functional features, as shown in FIG. 5, where the customized therapy is a formulation of microorganisms configured to correct dysbiosis characteristic of subjects having the identified characterization. As such, outputs of Block S140 can be used to directly promote a customized therapy formulation and regimen (e.g., dosage, usage instructions) to the subject based upon a trained therapy model. Additionally or alternatively, therapy provision can include recommendation of available therapeutic measures configured to shift microbiome composition and/or functional features toward a desired state. In variations, available therapeutic measures can include one or more of: consumables (e.g., food items, beverage items, etc.), topical therapies (e.g., lotions, ointments, antiseptics, etc.), nutritional supplements (e.g., vitamins, minerals, fiber, fatty acids, amino acids, prebiotics, etc.), medications, antibiotics, bacteriophages, and any other suitable therapeutic measure. For instance, a combination of commercially available probiotic supplements can include a suitable probiotic therapy for the subject according to an output of the therapy model.

Additionally or alternatively, in a specific example, the therapy of Block S110 can include a bacteriophage-based therapy. In more detail, one or more populations (e.g., in terms of colony forming units) of bacteriophages specific to a certain bacteria (or other microorganism) represented in the subject can be used to down-regulate or otherwise eliminate populations of the certain bacteria. As such, bacteriophage-based therapies can be used to reduce the size(s) of the undesired population(s) of bacteria represented in the subject. Complementarily, bacteriophage-based therapies can be used to increase the relative abundances of bacterial populations not targeted by the bacteriophage(s) used.

Therapy provision in Block S110 can include provision of notifications to a subject regarding the recommended therapy, other forms of therapy, headache-related characterizations, and/or other suitable headache-related data. Notifications can be provided to a subject by way of an electronic device (e.g., personal computer, mobile device, tablet, wearable, head-mounted wearable computing device, wrist-mounted wearable computing device, etc.) that executes an application, web interface, and/or messaging client configured for notification provision. In one example, a web interface of a personal computer or laptop associated with a subject can provide access, by the subject, to a user account of the subject, where the user account includes information regarding the user's characterization, detailed characterization of aspects of the user's microbiome, and notifications regarding suggested therapeutic measures generated in Blocks S140 and/or S110. In another example, an application executing at a personal electronic device (e.g., smart phone, smart watch, head-mounted smart device) can be configured to provide notifications (e.g., at a display, haptically, in an auditory manner, etc.) regarding therapy suggestions generated by the therapy model of Block S110. Notifications and/or probiotic therapies can additionally or alternatively be provided directly through an entity associated with a subject (e.g., a caretaker, a spouse, a significant other, a healthcare professional, etc.). In some further variations, notifications can additionally or alternatively be provided to an entity (e.g., healthcare professional) associated with a subject, where the entity is able to administer the therapy measure (e.g., by way of prescription, by way of conducting a therapeutic session, etc.). Notifications can, however, be provided for therapy administration to a subject in any other suitable manner.

3.8 Monitoring Therapy Effectiveness.

As shown in FIG. 7, the method can additionally or alternatively include Block S180, which recites: monitoring effectiveness of the therapy for the subject, based upon processing biological samples, to assess microbiome composition and/or functional features for the subject at a set of time points associated with the probiotic therapy. Block S180 can function to gather additional data regarding positive effects, negative effects, and/or lack of effectiveness of a probiotic therapy suggested by the therapy model for subjects of a given characterization. Monitoring of a subject during the course of a therapy promoted by the therapy model (e.g., by receiving and analyzing biological samples from the subject throughout therapy, by receiving survey-derived data from the subject throughout therapy) can thus be used to generate a therapy-effectiveness model for each characterization provided by the characterization process of Block S130, and each recommended therapy measure provided in Blocks S140 and S110.

In Block S180, the subject can be prompted to provide additional biological samples at one or more key time points of a therapy regimen that incorporates the therapy, and the additional biological sample(s) can be processed and analyzed (e.g., in a manner similar to that described in relation to Block S110) to generate metrics characterizing modulation of the subject's microbiome composition and/or functional features. For instance, metrics related to one or more of: a change in relative abundance of one or more taxonomic groups represented in the subject's microbiome at an earlier time point, a change in representation of a specific taxonomic group of the subject's microbiome, a ratio between abundance of a first taxonomic group of bacteria and abundance of a second taxonomic group of bacteria of the subject's microbiome, a change in relative abundance of one or more functional families in a subject's microbiome, and any other suitable metrics can be used to assess therapy effectiveness from changes in microbiome composition and/or functional features. Additionally or alternatively, survey-derived data from the subject, pertaining to experiences of the subject while on the therapy (e.g., experienced side effects, personal assessment of improvement, etc.) can be used to determine effectiveness of the therapy in Block S180. For example, the method 100 can include receiving a post-therapy biological sample from the user; collecting a supplementary dataset from the user, where the supplementary dataset describes user adherence to a therapy (e.g., a determined and promoted therapy); generating a post-therapy microbiome characterization of the first user in relation to the headache-related condition based on the headache-related condition characterization model and the post-therapy biological sample; and promoting an updated therapy to the user for the headache-related condition based on the post-therapy microbiome characterization (e.g., based on a comparison between the post-therapy microbiome characterization and a pre-therapy microbiome characterization; etc.) and the user adherence to the therapy (e.g., modifying the therapy based on positive or negative results for the user microbiome in relation to the headache-related condition; etc.). Therapy effectiveness, processing of additional biological samples (e.g., to determine additional headache-related characterizations, therapies, etc.), and/or other suitable aspects associated with continued biological sample collection, processing, and analysis in relation to headache-related conditions can be performed at any suitable time and frequency for generating, updating, and/or otherwise processing models (e.g., characterization models, therapy models, etc.), and/or for any other suitable purpose (e.g., as inputs associated with other portions of the method 100). However, Block S180 can be performed in any suitable manner.

The method 100 can, however, include any other suitable blocks or steps configured to facilitate reception of biological samples from subjects, processing of biological samples from subjects, analyzing data derived from biological samples, and generating models that can be used to provide customized diagnostics and/or probiotic-based therapeutics according to specific microbiome compositions and/or functional features of subjects.

The method 100 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which includes one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A method for characterizing a headache-related condition for a user, the method comprising:
   collecting samples from a set of users, wherein the samples comprise microorganism nucleic acids associated with the headache-related condition;
   determining microbiome composition diversity features and microbiome functional diversity features based on a microorganism sequence dataset derived from the microorganism nucleic acids;
   collecting supplementary data associated with the headache-related condition for the set of users;
   transforming the supplementary data, the microbiome composition diversity features, and the microbiome functional diversity features into a characterization model for the headache-related condition;
   generating a headache-related characterization for the user based on the characterization model; and
   providing a therapy to the user for the headache-related condition based on the headache-related characterization.

2. The method of claim 1,
   identifying a primer type for a microorganism nucleic acid sequence associated with the headache-related condition; and
   generating the microorganism sequence dataset based on the primer type and the microorganism nucleic acids.

3. The method of claim 2, wherein generating the microorganism sequence dataset comprises:
   fragmenting the microorganism nucleic acids; and
   performing multiplex amplification with the fragmented microorganism nucleic acids based on the fragmented microorganism nucleic acids and the identified primer type associated with the headache-related condition.

4. The method of claim 1,
   wherein collecting the samples from the set of users comprises providing a set of sampling kits to the set of users, each sampling kit of the set of sampling kits comprising a sample container operable to receive a sample; and
   wherein determining the microbiome composition diversity features and the microbiome functional diversity features comprises:
      generating the microorganism sequence dataset based on processing the microorganism nucleic acids with a bridge amplification substrate of a next generation sequencing platform of a sample handling system, and
      determining the microbiome composition diversity features and the microbiome functional diversity features at computing devices operable to communicate with the next generation sequencing platform.

5. The method of claim 1, wherein the therapy enables selective modulation of a microbiome of the user in relation to at least one of: a population size of a desired taxon, and a population size of a desired microbiome function, associated with improving a state of the headache-related condition.

6. The method of claim 1, wherein providing the therapy comprises providing at least one of a: medication type, a medication dosage, and a medication schedule, associated with a headache-related condition medication operable to improve a state of the headache-related condition.

7. The method of claim 1, wherein generating the headache-related characterization comprises generating the headache-related characterization based on a relative abundance characteristic associated with at least one of the microbiome composition diversity features and the microbiome functional diversity features, and wherein the method further comprises determining the relative abundance characteristic based on at least one of: a normalization, a feature vector derived from at least one of linear latent variable analysis and non-linear latent variable analysis, linear regression, non-linear regression, a kernel method, a feature embedding method, a machine learning method, and a statistical inference method.

8. The method of claim 1, wherein the headache-related condition comprises a migraine condition, and wherein generating the headache-related characterization for the user comprises generating a migraine characterization for the user based on user microbiome composition diversity features for the user, and wherein the user microbiome composition diversity features and the microbiome composition diversity features are associated with a set of taxa comprising at least one of: Ruminococcaceae (family), *Clostridium* (genera), and *Parabacteroides* (genera).

9. The method of claim 8, wherein generating the migraine characterization for the user comprises generating the migraine characterization based on the user microbiome composition diversity features and user microbiome functional diversity features, wherein the user microbiome functional diversity features and the microbiome functional diversity features are associated with at least one of: Carbohydrate Metabolism, Lipid Metabolism, Xenobiotics Biodegradation and Metabolism, Environmental Adaptation, Cell Motility, Enzyme Families, Metabolism of Cofactors and Vitamins, Nucleotide Metabolism, Replication and Repair, Pyruvate metabolism, Amino acid metabolism, Chloroalkane and chloroalkene degradation, Ribosome biogenesis in eukaryotes, Pentose and glucuronate interconversions, Terpenoid backbone biosynthesis, Biosynthesis and biodegradation of secondary metabolites, Riboflavin metabolism, Ribosome Biogenesis, Other transporters, Glyoxylate and dicarboxylate metabolism, Fructose and mannose metabolism, Chromosome, Galactose metabolism, One carbon pool by folate, Amino acid related enzymes, Pyrimidine metabolism, Ribosome, Aminoacyl-tRNA biosynthesis, Tuberculosis, Homologous recombination, Fatty acid biosynthesis, Cysteine and methionine metabolism, Plant-pathogen interaction, Pentose phosphate pathway, Peptidoglycan biosynthesis, Prenyltransferases, Translation factors, Translation proteins, Nicotinate and nicotinamide metabolism, Photosynthesis proteins, Photosynthesis, Phosphatidylinositol signaling system, DNA repair and recombination proteins, Nucleotide excision repair, Bacterial toxins, Bacterial chemotaxis, RNA polymerase, Naphthalene degradation, and Peptidases.

10. A method for characterizing a headache-related condition for a user, the method comprising:
   collecting a sample from the user, the sample comprising microorganism nucleic acids associated with the headache-related condition;
   determining a microorganism sequence dataset based on sample processing of the microorganism nucleic acids of the sample;
   determining microbiome features associated with the headache-related condition based on the microorganism sequence dataset;
   generating a headache-related characterization for the user based on the microbiome features and a headache-related condition characterization model; and providing a therapy to the user for the headache-related condition based on the headache-related characterization.

11. The method of claim 10, wherein generating the headache-related characterization comprises generating a migraine trigger profile for the user based on the microbiome features and the headache-related condition characterization model, wherein the therapy is operable to reduce at least one migraine trigger indicated by the migraine trigger profile for the user, and wherein providing the therapy comprises promoting the therapy operable to reduce the at least one migraine trigger indicated by the migraine trigger profile for the user.

12. The method of claim 11, further comprising detecting the at least one migraine trigger based on the migraine trigger profile and user supplementary data comprising at least one of motion sensor data and location sensor data collected from a mobile computing device associated with the user, wherein promoting the therapy operable to reduce the at least one migraine trigger comprises promoting the therapy in response to detecting the at least one migraine trigger.

13. The method of claim 10, further comprising after providing the therapy:
receiving a post-therapy sample from the user;
collecting a supplementary dataset from the user, wherein the supplementary dataset describes user adherence to the therapy;
generating a post-therapy microbiome characterization of the user in relation to the headache-related condition based on the headache-related condition characterization model and the post-therapy sample; and
promoting an updated therapy to the user for the headache-related condition based on the post-therapy microbiome characterization and the user adherence to the therapy.

14. The method of claim 10,
wherein the headache-related characterization comprises a microbiome diversity score correlated with the headache-related condition, and
wherein providing the therapy comprises promoting a nutrition-related therapy operable to improve the microbiome diversity score for improving a state of the headache-related condition, based on the headache-related characterization and nutrition-related supplementary data collected from the user.

15. The method of claim 10, wherein the microbiome features comprise at least one of a set of microbiome composition diversity features and a set of microbiome functional diversity features.

16. The method of claim 15, wherein generating the headache-related characterization for the user comprises generating the headache-related characterization based on the set of microbiome composition diversity features associated with at least one of: Ruminococcaceae (family), *Clostridium* (genera), and *Parabacteroides* (genera).

17. The method of claim 15, wherein generating the headache-related characterization for the user comprises generating the headache-related characterization based on the set of microbiome functional diversity features associated with at least one of: Carbohydrate Metabolism, Lipid Metabolism, Xenobiotics Biodegradation and Metabolism, Environmental Adaptation, Cell Motility, Enzyme Families, Metabolism of Cofactors and Vitamins, Nucleotide Metabolism, Replication and Repair, Pyruvate metabolism, Amino acid metabolism, Chloroalkane and chloroalkene degradation, Ribosome biogenesis in eukaryotes, Pentose and glucuronate interconversions, Terpenoid backbone biosynthesis, Biosynthesis and biodegradation of secondary metabolites, Riboflavin metabolism, Ribosome Biogenesis, Other transporters, Glyoxylate and dicarboxylate metabolism, Fructose and mannose metabolism, Chromosome, Galactose metabolism, One carbon pool by folate, Amino acid related enzymes, Pyrimidine metabolism, Ribosome, Aminoacyl-tRNA biosynthesis, Tuberculosis, Homologous recombination, Fatty acid biosynthesis, Cysteine and methionine metabolism, Plant-pathogen interaction, Pentose phosphate pathway, Peptidoglycan biosynthesis, Prenyltransferases, Translation factors, Translation proteins, Nicotinate and nicotinamide metabolism, Photosynthesis proteins, Photosynthesis, Phosphatidylinositol signaling system, DNA repair and recombination proteins, Nucleotide excision repair, Bacterial toxins, Bacterial chemotaxis, RNA polymerase, Naphthalene degradation, and Peptidases.

18. The method of claim 15, wherein determining the microbiome features comprises determining the set of microbiome composition diversity features and the set of microbiome functional diversity features based on the microorganism sequence dataset and a statistical analysis comprising at least one of: a prediction analysis, multi hypothesis testing, a random forest test, and principal component analysis.

19. The method of claim 10, wherein generating the headache-related characterization comprises generating the headache-related characterization based on the headache-related condition characterization model and the microbiome features associated with at least one of: presence of a microbiome feature from the microbiome features, absence of the microbiome feature from the microbiome features, relative abundance of different taxonomic groups associated with the headache-related condition, a ratio between at least two microbiome features associated with the different taxonomic groups, interactions between the different taxonomic groups, and phylogenetic distance between the different taxonomic groups.

20. The method of claim 10, further comprising:
determining a population microorganism sequence dataset for a population of users associated with the headache-related condition, based on a set of samples from the population of users and on a primer type associated with the headache-related condition;
collecting a supplementary dataset associated with diagnosis of the headache-related condition for the population of users; and
generating the headache-related condition characterization model based on the population microorganism sequence dataset and the supplementary dataset.

* * * * *